(12) United States Patent
Blain et al.

(10) Patent No.: US 10,646,351 B2
(45) Date of Patent: May 12, 2020

(54) EXPANDABLE INTERBODY DEVICE

(71) Applicant: Spinal Elements, Inc., Carlsbad, CA (US)

(72) Inventors: Jason Blain, Encinitas, CA (US); David Solum, San Jose, CA (US); Dean Johnson, Solano Beach, CA (US); Markanthony Flores, Chula Vista, CA (US)

(73) Assignee: Spinal Elements, Inc., Carlsbad, CA (US)

( * ) Notice: Subject to any disclaimer, the term of this patent is extended or adjusted under 35 U.S.C. 154(b) by 44 days.

(21) Appl. No.: 16/049,503

(22) Filed: Jul. 30, 2018

(65) Prior Publication Data

US 2018/0333273 A1 Nov. 22, 2018

Related U.S. Application Data

(63) Continuation of application No. 15/608,079, filed on May 30, 2017, now Pat. No. 10,034,765, which is a
(Continued)

(51) Int. Cl.
*A61F 2/44* (2006.01)
*A61F 2/30* (2006.01)
*A61F 2/46* (2006.01)

(52) U.S. Cl.
CPC ........ *A61F 2/4455* (2013.01); *A61F 2/30771* (2013.01); *A61F 2/441* (2013.01); *A61F 2/447* (2013.01); *A61F 2/4611* (2013.01); *A61F 2/4603* (2013.01); *A61F 2002/3006* (2013.01); *A61F 2002/3008* (2013.01);
(Continued)

(58) Field of Classification Search
CPC ...... A61F 2/4455; A61F 2/446; A61F 2/4465; A61F 2/447
See application file for complete search history.

(56) References Cited

U.S. PATENT DOCUMENTS

| 5,522,899 A | 6/1996 | Michelson |
| 5,658,335 A | 8/1997 | Allen |

(Continued)

FOREIGN PATENT DOCUMENTS

| JP | 2013539396 | 10/2013 |
| WO | 9700054 | 1/1997 |

(Continued)

OTHER PUBLICATIONS

Official Communication (EESR) in European Application No. 14868605.8, dated Jun. 21, 2017.
(Continued)

*Primary Examiner* — Si Ming Ku

(57) ABSTRACT

An expandable interbody device for placement between adjacent vertebrae having an upper structure, a lower structure and a screw mechanism, wherein actuation of the screw mechanism moves the upper and lower structures between a collapsed configuration and an expanded configuration. A deployment tool couples to the expandable interbody device for positioning the device between adjacent vertebrae, actuating the screw mechanism and delivering a material to a chamber of the expandable interbody device.

14 Claims, 23 Drawing Sheets

Related U.S. Application Data continuation of application No. 14/333,336, filed on Jul. 16, 2014, now Pat. No. 9,668,876.

(60) Provisional application No. 61/912,360, filed on Dec. 5, 2013, provisional application No. 61/912,432, filed on Dec. 5, 2013.

(52) U.S. Cl.
CPC ......... *A61F 2002/3092* (2013.01); *A61F 2002/3093* (2013.01); *A61F 2002/30217* (2013.01); *A61F 2002/30281* (2013.01); *A61F 2002/30367* (2013.01); *A61F 2002/30405* (2013.01); *A61F 2002/30408* (2013.01); *A61F 2002/30556* (2013.01); *A61F 2002/30579* (2013.01); *A61F 2002/30593* (2013.01); *A61F 2002/30601* (2013.01); *A61F 2002/30774* (2013.01); *A61F 2002/30785* (2013.01); *A61F 2002/30828* (2013.01); *A61F 2002/30878* (2013.01); *A61F 2002/30904* (2013.01); *A61F 2002/4622* (2013.01); *A61F 2002/4627* (2013.01); *A61F 2310/00017* (2013.01); *A61F 2310/00023* (2013.01); *A61F 2310/00029* (2013.01); *A61F 2310/00179* (2013.01); *A61F 2310/00203* (2013.01); *A61F 2310/00239* (2013.01); *A61F 2310/00407* (2013.01)

(56) References Cited

U.S. PATENT DOCUMENTS

| | | | |
|---|---|---|---|
| 6,080,193 A | 6/2000 | Hochshuler et al. | |
| 6,176,882 B1 | 1/2001 | Biedermann et al. | |
| 6,454,806 B1 | 9/2002 | Cohen et al. | |
| 6,641,614 B1 | 11/2003 | Wagner et al. | |
| 6,648,917 B2 | 11/2003 | Gerbec et al. | |
| 6,685,742 B1 | 2/2004 | Jackson | |
| 6,719,796 B2 | 4/2004 | Cohen et al. | |
| 6,835,206 B2 | 12/2004 | Jackson | |
| 6,852,129 B2 | 2/2005 | Gerbec et al. | |
| 7,837,734 B2 | 11/2010 | Zucherman et al. | |
| 7,850,733 B2 | 12/2010 | Baynham et al. | |
| 8,062,375 B2 | 11/2011 | Glerum et al. | |
| 8,105,382 B2 | 1/2012 | Olmos et al. | |
| 8,187,332 B2 | 5/2012 | McLuen | |
| 8,192,495 B2 | 6/2012 | Simpson et al. | |
| 8,267,939 B2 | 9/2012 | Cipoletti et al. | |
| 8,366,777 B2 | 2/2013 | Matthis et al. | |
| 8,398,713 B2 | 3/2013 | Weiman | |
| 8,435,298 B2 | 5/2013 | Weiman | |
| 8,444,697 B1 | 5/2013 | Butler et al. | |
| 8,491,659 B2 | 7/2013 | Weiman | |
| 8,535,380 B2 | 9/2013 | Greenhalgh et al. | |
| 8,597,360 B2 | 12/2013 | McLuen et al. | |
| 8,603,170 B2 | 12/2013 | Cipoletti et al. | |
| 2004/0254643 A1 | 12/2004 | Jackson | |
| 2005/0125061 A1 | 6/2005 | Zucherman et al. | |
| 2008/0140207 A1* | 6/2008 | Olmos | A61F 2/4611 623/17.16 |
| 2010/0145455 A1 | 6/2010 | Simpson et al. | |
| 2010/0211176 A1 | 8/2010 | Greenhalgh | |
| 2011/0130835 A1 | 6/2011 | Ashley et al. | |
| 2011/0172774 A1 | 7/2011 | Varela | |
| 2012/0035729 A1 | 2/2012 | Glerum et al. | |
| 2012/0059470 A1 | 3/2012 | Weiman | |
| 2012/0059475 A1 | 3/2012 | Weiman | |
| 2012/0185049 A1 | 7/2012 | Varela | |
| 2012/0203347 A1 | 8/2012 | Glerum et al. | |
| 2012/0226357 A1 | 9/2012 | Varela | |
| 2012/0323328 A1 | 12/2012 | Weiman | |
| 2012/0330421 A1 | 12/2012 | Weiman | |
| 2012/0330422 A1 | 12/2012 | Weiman | |
| 2013/0023993 A1 | 1/2013 | Weiman | |
| 2013/0123924 A1 | 5/2013 | Butler et al. | |
| 2013/0158669 A1 | 6/2013 | Sungarian et al. | |
| 2013/0173003 A1 | 7/2013 | Matthis et al. | |
| 2013/0197647 A1 | 8/2013 | Wolters et al. | |
| 2013/0204371 A1 | 8/2013 | McLuen et al. | |
| 2013/0211525 A1 | 8/2013 | McLuen et al. | |
| 2013/0211526 A1 | 8/2013 | Alheidt et al. | |

FOREIGN PATENT DOCUMENTS

| | | |
|---|---|---|
| WO | 2012031267 | 3/2012 |
| WO | 2013025876 | 2/2013 |
| WO | 2013049758 | 4/2013 |

OTHER PUBLICATIONS

International Search Report and Written Opinion for International Application No. PCT/US2014/068652, dated Apr. 17, 2015.

\* cited by examiner

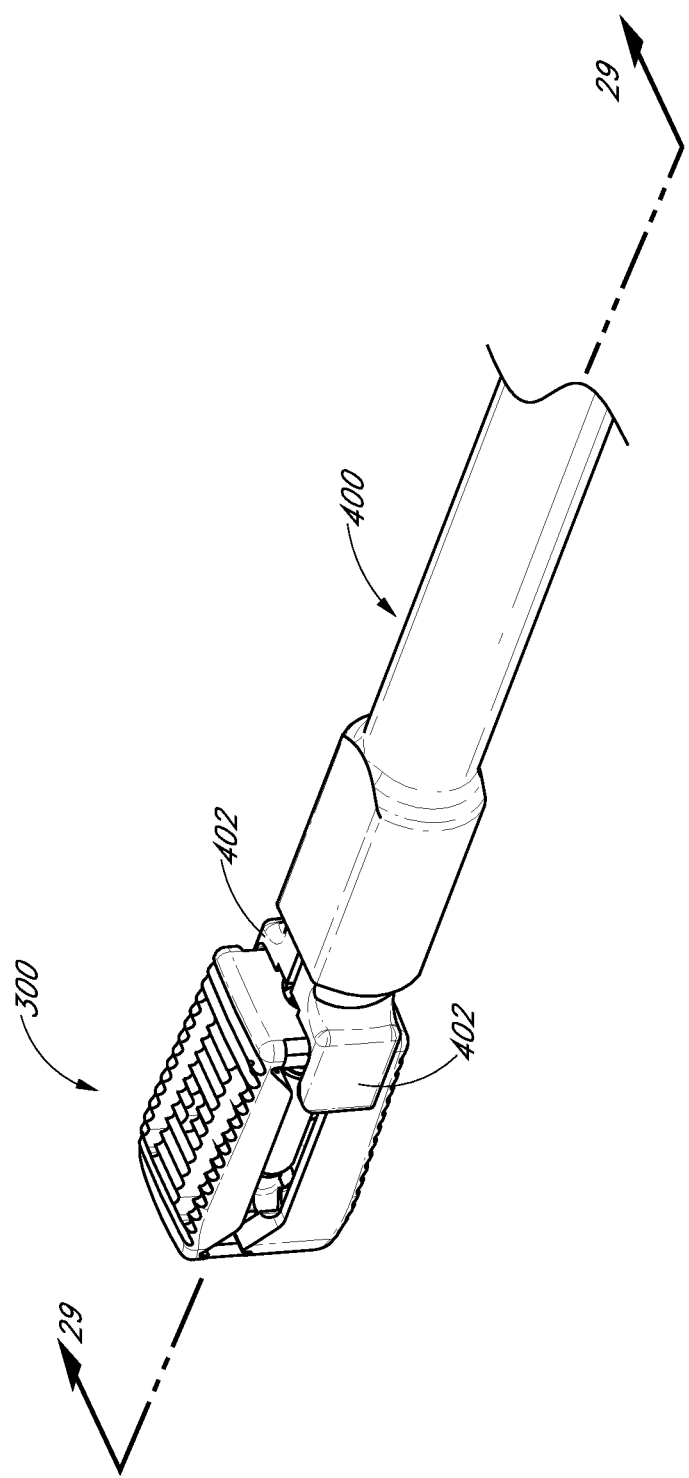

EXPANDABLE INTERBODY DEVICE

CROSS-REFERENCE TO RELATED APPLICATIONS

Any and all applications for which a foreign or domestic priority claim is identified in the Application Data Sheet as filed with the present application are hereby incorporated by reference under 37 CFR 1.57, including U.S. patent application Ser. No. 15/608,079, filed May 30, 2017, U.S. patent application Ser. No. 14/333,336, filed Jul. 16, 2014, now U.S. Pat. No. 9,668,876, U.S. Provisional Application No. 61/912,360, filed Dec. 5, 2013 and U.S. Provisional Application No. 61/912,432, filed Dec. 5, 2013.

BACKGROUND

Field

The present disclosure generally relates to the field of spinal orthopedics, and more particularly to expandable spinal implants for placement in intervertebral spaces between adjacent vertebrae.

Related Art

The spine is a flexible structure that extends from the base of the skull to the tailbone. The weight of the upper body is transferred through the spine to the hips and the legs. The spine contains a plurality of bones called vertebrae. The vertebrae are hollow and stacked one upon the other, forming a strong hollow column for support. The hollow core of the spine houses and protects the nerves of the spinal cord. The spine is held upright through the work of the back muscles, which are attached to the vertebrae. While the normal spine has no side-to-side curve, it does have a series of front-to-back curves, giving it a gentle "S" shape.

Each vertebra is separated from the vertebra above or below by a cushion-like, fibrocartilage called an intervertebral disc. The discs act as shock absorbers, cushioning the spine, and preventing individual bones from contacting each other. In addition, intervertebral discs act as a ligament that holds vertebrae together. Intervertebral discs also work with the facet joint to allow for slight movement of the spine. Together, these structures allow the spine to bend, rotate and/or twist.

The spinal structure can become damaged as a result of degeneration, dysfunction, disease and/or trauma. More specifically, the spine may exhibit disc collapse, abnormal curvature, asymmetrical disc space collapse, abnormal alignment of the vertebrae and/or general deformity, which may lead to imbalance and tilt in the vertebrae. This may result in nerve compression, disability and overall instability and pain. If the proper shaping and/or curvature are not present due to scoliosis, neuromuscular disease, cerebral palsy, or other disorder, it may be necessary to straighten or adjust the spine into a proper curvature with surgery to correct these spinal disorders.

Surgical treatments may involve manipulation of the spinal column by attaching a corrective device, such as rods, wires, hooks or screws, to straighten abnormal curvatures, appropriately align vertebrae of the spinal column and/or reduce further rotation of the spinal column. The correct curvature is obtained by manipulating the vertebrae into their proper position and securing that position with a rigid system of screws and rods. The screws may be inserted into the pedicles of the vertebrae to act as bone anchors, and the rods may be inserted into heads of the screws. Two rods may run substantially parallel to the spine and secure the spine in the desired shape and curvature. Thus the rods, which are shaped to mimic the correct spinal curvature, force the spine into proper alignment. Bone grafts are then placed between the vertebrae and aid in fusion of the individual vertebrae together to form a correctly aligned spine.

Other ailments of the spine result in degeneration of the spinal disc in the intervertebral space between adjacent vertebrae. Disc degeneration can cause pain and other complications. Conservative treatment can include non-operative treatment requiring patients to adjust their lifestyles and submit to pain relievers and a level of underlying pain. Operative treatment options include disc removal. This can relieve pain in the short term, but also often increases the risk of long-term problems and can result in motor and sensory deficiencies resulting from the surgery. Disc removal and more generally disc degeneration disease are likely to lead to a need for surgical treatment in subsequent years. The fusion or fixation will minimize or substantially eliminate relative motion between the fixed or fused vertebrae. In surgical treatments, interbody implants may be used to correct disc space collapse between adjacent vertebra, resulting in spinal fusion of the adjacent vertebra.

A fusion is a surgical method wherein two or more vertebrae are joined together (fused) by way of interbody implants, sometimes with bone grafting, to form a single bone. The current standard of care for interbody fusion requires surgical removal of all or a portion of the intervertebral disc. After removal of the intervertebral disc, the interbody implant is implanted in the interspace. In many cases, the fusion is augmented by a process called fixation. Fixation refers to the placement of screws, rods, plates, or cages to stabilize the vertebrae so that fusion can be achieved.

Interbody implants must be inserted into the intervertebral space in the same dimensions as desired to occupy the intervertebral space after the disc is removed. This requires that an opening sufficient to allow the interbody implant must be created through surrounding tissue to permit the interbody implant to be inserted into the intervertebral space. In some cases, the intervertebral space may collapse prior to insertion of the interbody implant. In these cases, additional hardware may be required to increase the intervertebral space prior to insertion of the implant.

In addition, minimally invasive surgical techniques have been used on the spine. Under minimally invasive techniques, access to the intervertebral space is taken to reach the spine through small incisions. Through these incisions, discs are removed and an interbody implant is placed in the intervertebral disc space to restore normal disc height. Minimally invasive spine surgery offers multiple advantages as compared to open surgery. Advantages include: minimal tissue damage, minimal blood loss, smaller incisions and scars, minimal post-operative discomfort, and relative quick recovery time and return to normal function.

SUMMARY

It would be desirable to insert an interbody device with a first smaller dimension into an intervertebral space and once in place, deploy to a second, relatively larger dimension to occupy the intervertebral space. This first smaller dimension can permit the use of minimally invasive surgical techniques for easy access to the intervertebral space, which can cause less disruption of soft and boney tissue in order to get to the intervertebral space. The interbody device may be implanted with or without the need of additional hardware.

Disclosed is an expandable interbody device that is configured to have an initial collapsed configuration having a first height suitable for being inserted into an intervertebral space between a pair of adjacent vertebrae, and an expanded configuration having a second height that is greater than the first height. The implant can be expanded from the initial collapsed configuration to the expanded configuration in-situ. The expanded configuration can provide support to the adjacent vertebrae while bone fusion occurs and can also provide rigid support between the adjacent vertebrae that withstands compressive forces. In some configurations, the expandable interbody device can help increase the distance between the adjacent vertebrae. By inserting the expandable interbody device in the initial collapsed configuration into the intervertebral space, it is possible to perform the surgery percutaneously with minimal disruption to tissues surrounding the surgical site and intervening soft tissue structures. The expandable interbody device can be implanted through a minimally invasive or an open wound procedure.

In accordance with at least one of the embodiments disclosed herein, an expandable interbody device for placement between adjacent vertebrae can comprise an upper structure comprising an upper proximal angled surface and an upper distal angled surface; a lower structure comprising a lower proximal angled surface and a lower distal angled surface, the lower structure configured to slideably couple with the upper structure; and a screw mechanism between the upper structure and the lower structure. The screw mechanism can comprise a proximal section comprising a proximal frustoconical surface, a distal section comprising a distal frustoconical surface, and a coupler comprising a proximal side configured to engage the proximal section and a distal side configured to engage the distal section, wherein the proximal section and the distal section are configured to rotate as a unit to change a length of the screw mechanism from a first length to a second length. The proximal frustoconical surface can be configured to engage the upper proximal angled surface and the lower proximal angled surface, and the distal frustoconical surface can be configured to engage the upper distal angled surface and the lower distal angled surface to move the upper structure and the lower structure from a first distance to a second distance.

The coupler can further comprise at least one anti-rotational feature configured to engage the upper structure or lower structure to prevent the coupler from rotating when the proximal section and the distal section are rotated.

The proximal section can comprise first threads wound in a first direction configured to engage a proximal threaded hole in the coupler, and the distal section can comprise second threads wound in a second direction, opposite the first direction, configured to engage a distal threaded hole in the coupler. In some embodiments, the first threads and the second threads have an equal pitch, such that when the screw mechanism is actuated, a proximal end of the interbody device changes height at the same rate as a distal end of the interbody device. In other embodiments, the first threads and the second threads have a different pitch, such that when the screw mechanism is actuated, a proximal end of the interbody device changes height at a different rate than a distal end of the interbody device.

The upper structure and lower structure can further comprise a plurality of protrusions or teeth. The upper structure and/or the lower structure can comprise vertebrae engagement surfaces with a porous or roughened surface. For example, the vertebrae engagement surfaces can comprise a titanium coating.

In some embodiments, the proximal section comprises at least one hole in fluid communication with a drive interface and an interior cavity of the interbody device. The interbody device can further comprise at least one recess configured to couple with a deployment tool, the at least one recess comprising a hole in fluid communication with an interior cavity of the interbody device.

In some embodiments, the distal section comprises a keyed shaft configured to slideably engage with a matching keyed bore on the proximal section.

In accordance with at least one of the embodiments disclosed herein, an expandable interbody device for placement between adjacent vertebrae can comprise an upper structure, a lower structure configured to slideably couple with the upper structure, and a screw mechanism between the upper structure and the lower structure, the screw mechanism comprising a proximal section and a distal section that are configured to rotate as a unit to change a length of the screw mechanism from a first length to a second length, wherein the change in the length of the screw mechanism causes the distance between the upper structure and the lower structure to change from a first distance to a second distance to form a chamber to be filled by one or more of fluids, medication, bone graft material, allograft and Demineralized Bone Matrix.

In accordance with at least one of the embodiments disclosed herein, a kit for performing spinal stabilization can comprise an expandable interbody device for placement between adjacent vertebrae, wherein in an expanded configuration the expandable interbody device comprises a chamber, and a deployment tool for delivering the expandable interbody device between adjacent vertebrae, the deployment tool comprising a distal portion that is releasably attachable to the expandable interbody device and a proximal portion configured to extend outside a surgical incision. The proximal portion can comprise an opening to a channel that extends through the deployment tool and is in fluid communication with the distal portion of the deployment tool, the channel capable of transporting a material from outside the incision into the chamber of the expandable interbody device.

In some embodiments, a proximal section of the expandable interbody device comprises at least one hole in fluid communication with the chamber. The expandable interbody device can further comprise at least one recess with a hole that is in fluid communication with the chamber. The deployment tool can comprise arms that are configured to attach to the at least one recess and further comprise one or more channels extending to the tips of the arms to deliver material through the at least one recess into the chamber of the expandable interbody device.

In accordance with at least one of the embodiments disclosed herein, a method of implanting an expandable interbody device between adjacent vertebrae can comprise positioning the expandable interbody device between adjacent vertebrae. The expandable interbody device can comprise an upper structure, a lower structure configured to slideably couple with the upper structure, and a screw mechanism between the upper structure and the lower structure. The method can further comprise rotating the screw mechanism to change a length of the screw mechanism from a first length to a second length which causes the distance between the upper structure and the lower structure to change from a first distance to a second distance to form a chamber, and injecting material into the chamber.

In some embodiments, the first distance corresponds to a collapsed configuration with the upper structure adjacent the lower structure and the second distance corresponds to an expanded configuration with the upper structure separated from the lower structure.

The screw mechanism can comprise a proximal section comprising a proximal frustoconical surface, a distal section comprising a distal frustoconical surface, and a coupler comprising a proximal side configured to engage the proximal section and a distal side configured to engage the distal section.

The material can be one or more of fluids, medication, bone graft material, allograft and Demineralized Bone Matrix.

In some embodiments, the expandable interbody device can be positioned between the adjacent vertebrae using a deployment tool that extends from the vertebrae to outside an incision.

The step of injecting the material can comprise delivering the material through a channel extending through the deployment tool.

In accordance with at least one of the embodiments disclosed herein, an expandable interbody device for placement between adjacent vertebrae can comprise an outer structure having a central opening and front and back sides with opposed front and back openings, an inner structure configured to slideably fit vertically within the outer structure central opening, the inner structure having a central opening and front and back sides with opposed front and back threaded holes axially aligned with the opposed front and back openings of the outer structure, and a variable length screw mechanism having proximal and distal heads slideably engaged to the front and back openings of the outer structure, and proximal and distal threaded shafts threadably coupled to the front and back threaded holes of the inner structure, wherein rotation of the screw mechanism changes a length of the screw mechanism from a first length to a second length and the proximal and distal heads compress against the front and back openings resulting in vertical translation of the inner structure relative to the outer structure from a first height to a second height.

The first height can be a collapsed configuration with the inner structure within the outer structure central opening and the second height can be an expanded configuration with the inner structure extending vertically out of the outer structure central opening.

The threaded shafts can comprise proximal threads threadably coupled to the front threaded hole with first threads in a first direction, and distal threads threadably coupled to the back threaded hole with second threads in a second direction, opposite the first direction, such that when the screw mechanism is rotated, the length of the screw mechanism increases or decreases. In some embodiments, the first and second threads have an equal pitch, such that when the screw mechanism is rotated the vertical translation of a proximal end and a distal end of the inner structure moves at a same rate relative to a proximal end and a distal end of the outer structure. In other embodiments, the first and second threads have a different pitch, such that when the screw mechanism is rotated the vertical translation of a proximal end of the inner structure relative to the outer structure moves at a different rate than a distal end of the inner structure relative to the outer structure.

In some embodiments, the front and back openings of the outer structure comprise ramp portions and the proximal and distal heads of the variable length screw mechanism can be configured to engage and slide along the ramp portions during translation of the inner structure relative to the outer structure. In other embodiments, the front and back openings of the outer structure have non-complementary engagement surfaces with the proximal and distal heads of the variable length screw mechanism, and the proximal and distal heads of the variable length screw mechanism are configured to engage and slide along the non-complementary engagement surfaces during translation of the inner structure relative to the outer structure.

The interbody device can further comprise a keyed internal bore on the distal end of the proximal shaft, and a keyed outer surface on the proximal end of the distal shaft configured to slidingly engage with the keyed internal bore of the proximal shaft, wherein the keyed outer surface slides within the keyed internal bore to allow the screw mechanism to have a variable length. The outer structure and inner structure can further comprise a plurality of protrusions or teeth.

In some embodiments, the vertebrae engagement surfaces comprise a porous or roughened surface that may be formed of a porous material, coated with a porous material, or chemically etched to form a porous or roughened surface with pores for bone growth with the adjacent vertebra.

In accordance with at least one of the embodiments disclosed herein, an expandable interbody device for placement between adjacent vertebrae can comprise an outer structure having an outer wall enclosing a central opening, the outer wall having front and back sides with opposed front and back openings, an inner structure having an inner wall with a lower flanged portion enclosing a central opening, the inner wall being configured to slideably fit vertically within the outer structure central opening, the inner wall having front and back slots with ramps proximate the slots within the inner structure central opening, the front and back slots being axially aligned with the opposed front and back openings of the outer structure, and a screw mechanism coupled to the inner and outer structures. The screw mechanism can comprise a shaft with proximal and distal portions, and proximal and distal threaded ramped components threadably coupled to the proximal and distal portions, the ramped components being configured to slideably engage the ramps on the front and back sides of the inner structure during expansion of the screw mechanism. Rotation of the expansion screw mechanism can change a distance between the proximal and distal ramped components from a first length to a second length and the proximal and distal ramped components slide against the front and back ramps resulting in vertical translation of the inner structure relative to the outer structure from a first height to a second height.

The proximal and distal portions of the shaft can comprise proximal and distal ends positioned within the front and back openings of the outer structure. A proximal end of the shaft can comprise a tool engagement portion.

The shaft can comprise proximal threads threadably coupled to the proximal threaded ramped component with first threads in a first direction, and distal threads threadably coupled to the distal threaded ramped component with second threads in a second direction, opposite the first direction, such that when the screw mechanism is rotated, the distance between the proximal and distal ramped components increases or decreases.

In some embodiments, the first and second threads have an equal pitch, such that when the screw mechanism is rotated the vertical translation of a proximal end and a distal end of the inner structure moves at a same rate relative to a proximal end and a distal end of the outer structure. In other embodiments, the first and second threads have different pitches, such that when the screw mechanism is rotated the vertical translation of a proximal end of the inner structure relative to the outer structure moves at a different rate than a distal end of the inner structure relative to the outer structure.

The outer structure and inner structure can further comprise a plurality of protrusions or teeth. The vertebrae engagement surfaces can comprise a porous or roughened surface that may be formed of a porous material, coated with a porous material, or chemically etched to form a porous or roughened surface with pores for bone growth with the adjacent vertebra.

In accordance with at least one of the embodiments disclosed herein, a deployment tool for delivering an expandable interbody device between adjacent vertebrae can comprise a distal portion configured to releasably couple to the expandable interbody device, a proximal portion comprising a mechanism for coupling and releasing the expandable interbody device, and an actuation device capable of expanding the interbody device from a first configuration to a second configuration, wherein the proximal portion is configured to extend outside a surgical incision, wherein the proximal portion comprises an opening to a channel that extends through the deployment tool and is in fluid communication with the distal portion of the deployment tool, the channel capable of transporting a material from outside the incision into the expandable interbody device.

The distal portion can comprise arms configured to couple to at least one recess on the expandable interbody device. The arms can comprise one or more channels extending to the tips of the arms to deliver material through the at least one recess into a chamber of the expandable interbody device. The actuation device can comprise a shaft that extends through the deployment tool to drive the expandable interbody device at the distal portion by manipulating an actuator at the proximal portion.

BRIEF DESCRIPTION OF THE DRAWINGS

Specific embodiments and modifications thereof will become apparent to those skilled in the art from the detailed description herein having reference to the figures that follow, of which:

FIG. 26 is a close-up perspective view of the expandable interbody device and deployment tool of FIG. 22.

DETAILED DESCRIPTION

Figure 1:
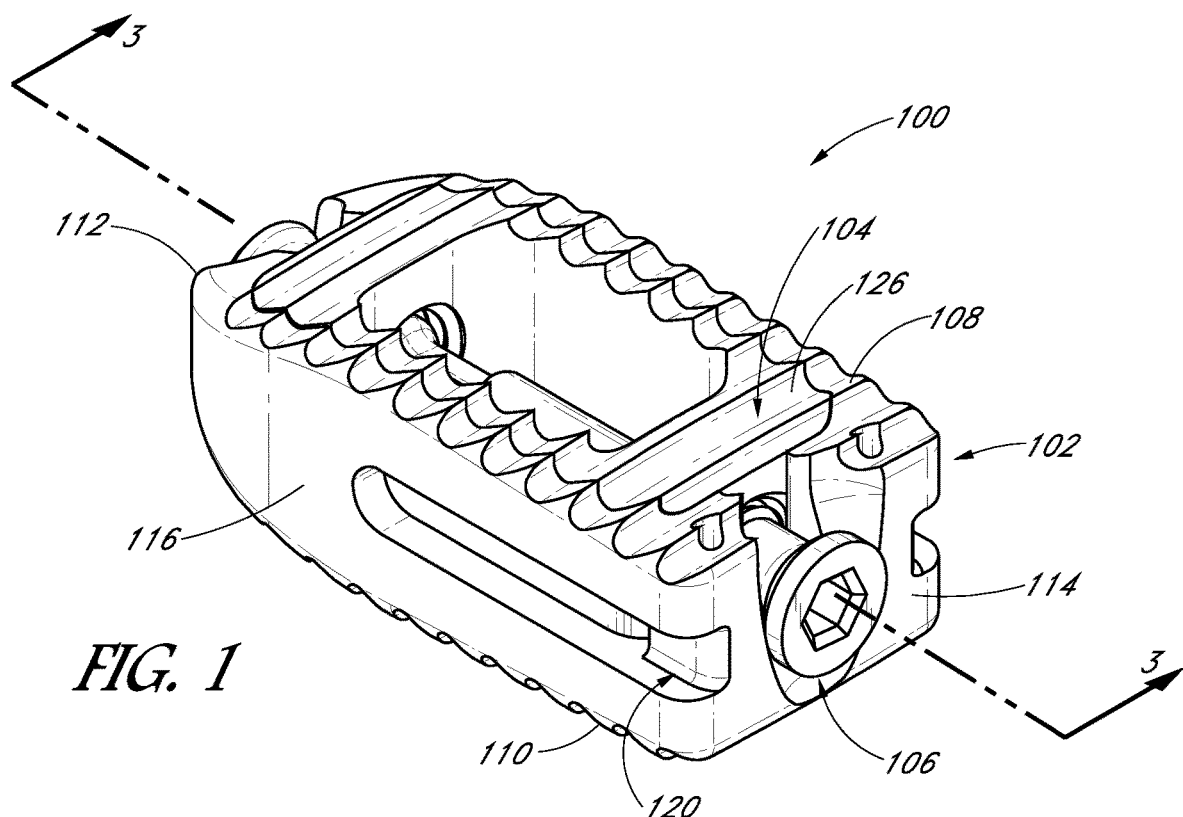
FIG. 1 is a perspective view showing an expandable interbody device in a collapsed configuration, according to an embodiment of the present invention.
Figure 2:
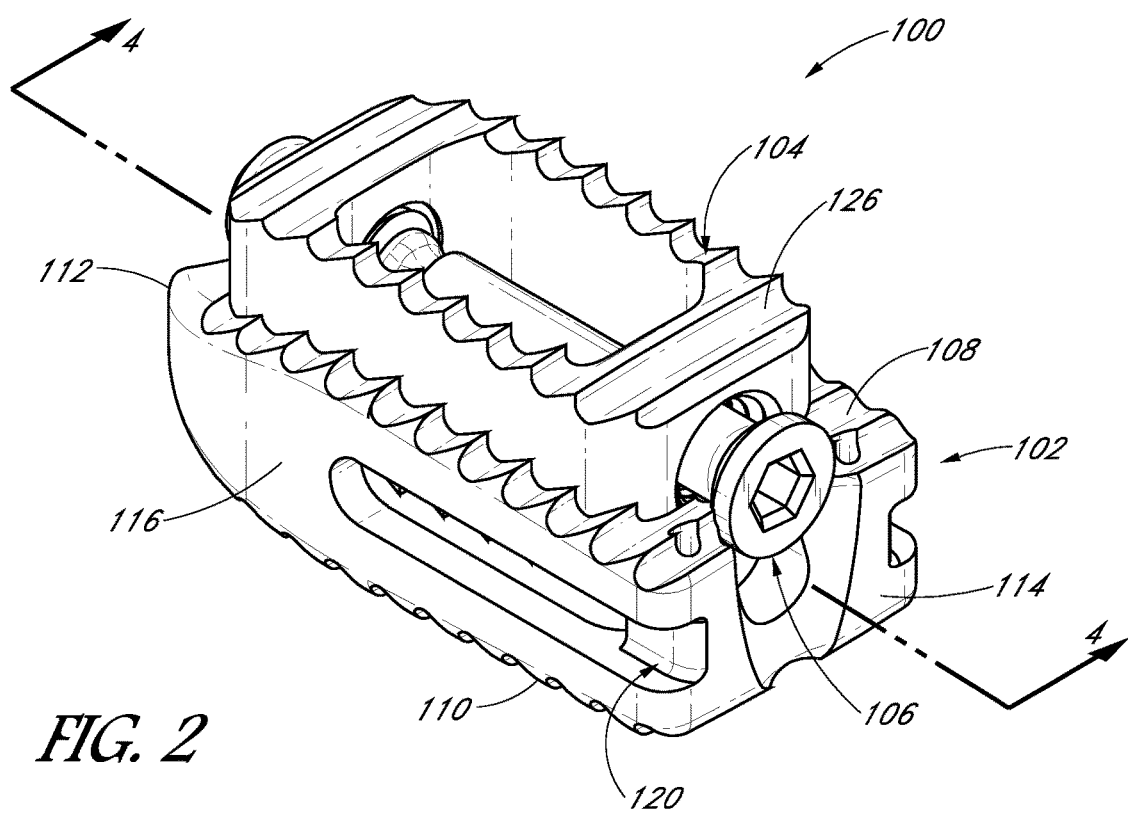
FIG. 2 is a perspective view showing the expandable interbody device of FIG. 1 in an expanded configuration.

An expandable interbody device can be configured to have an initial collapsed configuration having a first height suitable for being inserted into an intervertebral space between a pair of adjacent vertebrae, and an expanded configuration having a second height that is greater than the first height. The implant can be expanded from the initial collapsed configuration to the expanded configuration in-situ. The use of a small interbody implant which may be expanded in-situ allows the possibility of performing the surgery percutaneously with minimal disruption to tissues surrounding the surgical site and intervening soft tissue structures, through a minimally invasive or open procedure. The expandable interbody device of the present disclosure can include features that reduce displacement of soft tissue and structures during placement of the expandable interbody device while providing support after placement to the adjacent vertebrae while bone fusion occurs. The expandable interbody device includes a collapsed configuration with dimensions that can allow insertion of the expandable interbody device between the vertebrae. Once the expandable interbody device is positioned in a desired location between the vertebrae, the expandable interbody device may be expanded to an expanded configuration. The expanded configuration can increase the distance between the adjacent vertebrae and provide support to the adjacent vertebrae while bone fusion occurs. The expanded configuration can also provide rigid support between the adjacent vertebrae that withstands compressive forces. The expandable interbody device of the present disclosure may sometimes be referred to as an expandable interbody implant, expandable interbody spacer or expandable corpectomy device, all of which are envisioned for the present disclosure.

Several non-limiting embodiments will now be described with reference to the figures, wherein like numerals reflect like elements throughout. The terminology used in the description presented herein is not intended to be interpreted in any limited or restrictive way, simply because it is being utilized in conjunction with a detailed description of certain specific embodiments. Furthermore, some embodiments may include several novel features, no single one of which is solely responsible for its desirable attributes or which is essential to the devices and methods described herein.

The words proximal and distal are applied herein to denote specific ends of components of the instrument described herein. A proximal end refers to the end of a component nearer to an operator of the instrument when the instrument is being used. A distal end refers to the end of a component further from the operator and extending towards the surgical area of a patient and/or the implant. The words top, bottom, left, right, upper and lower are used herein to refer to sides of the device from the described point of view. These reference descriptions are not intended to limit the orientation of the implanted interbody device and the device can be positioned in any functional orientation. For example, in some configurations, the interbody device can be used in an upside-down orientation from the specific orientation described herein.

Referring now to FIGS. 1-6, an expandable interbody device 100 can be a spinal implant that includes an outer structure 102, an inner structure 104, and a screw mechanism 106. The expandable interbody device 100 can be movable between a collapsed configuration (shown in FIG. 1) to an expanded configuration (shown in FIG. 2) utilizing the screw mechanism 106.

Figure 3:
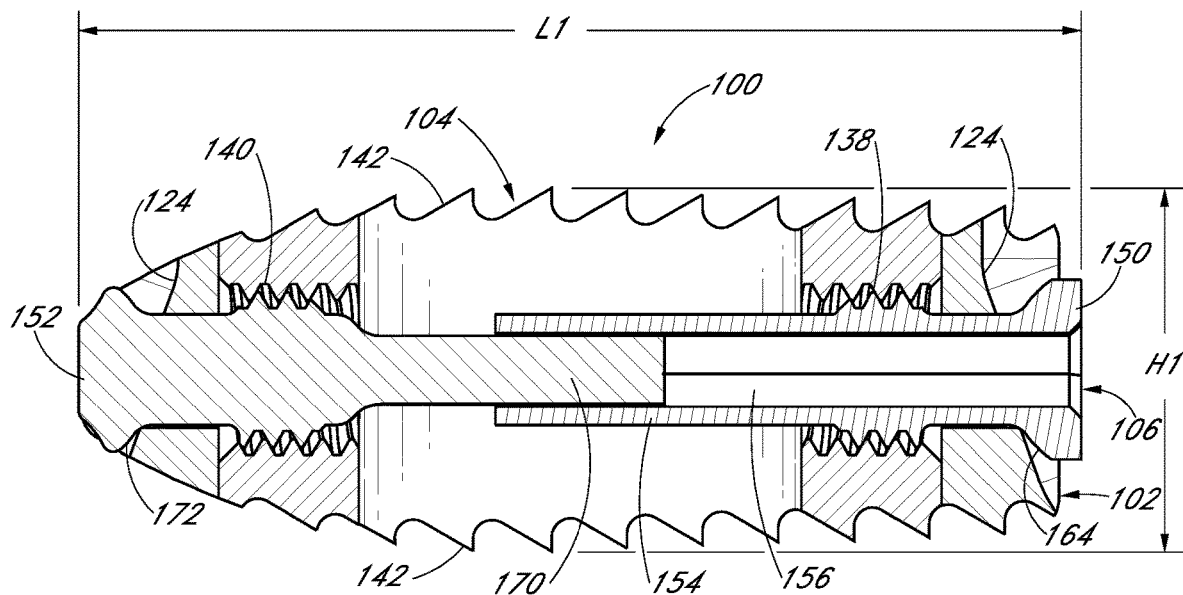
FIG. 3 is a cross-sectional view of the expandable interbody device of FIG. 1 in a collapsed configuration.
Figure 4:
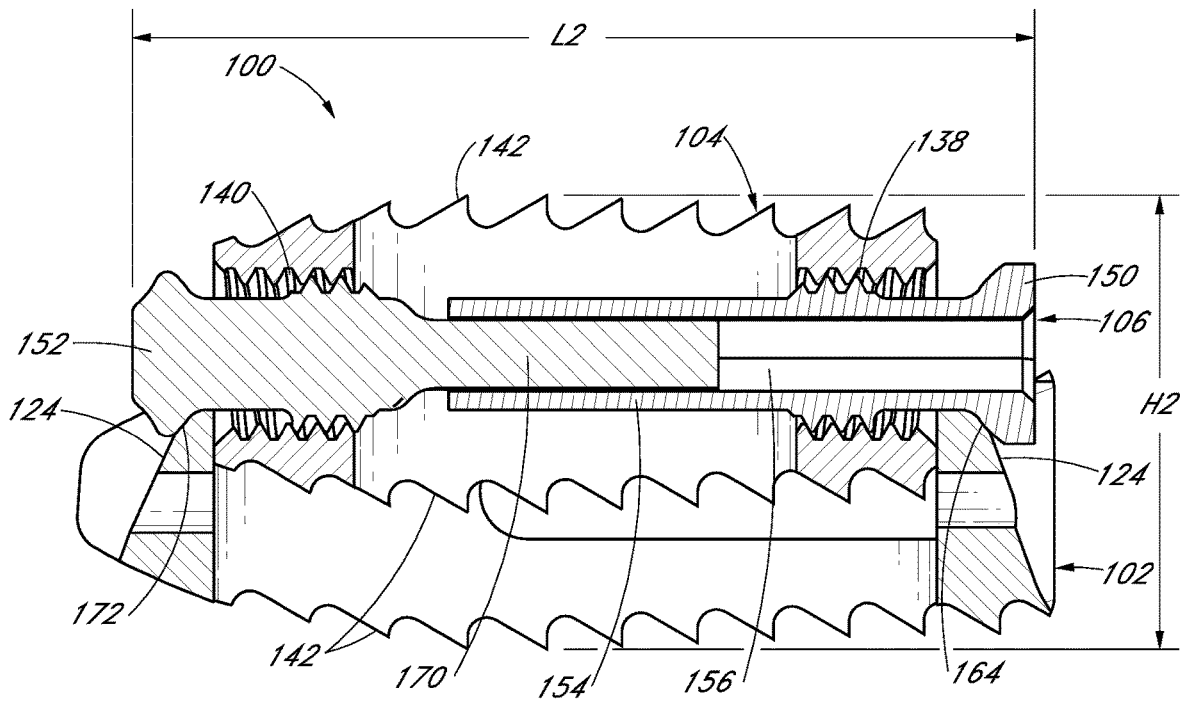
FIG. 4 is a cross-sectional view of the expandable interbody device of FIG. 2 in an expanded configuration.

The outer structure 102 can include a top surface 108, a bottom surface 110, a front side 112, a back side 114, and left and right sides 116. A combination of the sides 112, 114 and 116 forms a wall that encloses a central opening 118. The front side 112, back side 114, left and right sides 116 may have a varying height, length, thickness, and/or curvature radius. The left and right sides 116 may include longitudinal openings, slots or trenches 120 configured to interface with an insertion and/or deployment tool (not shown) during implantation and deployment of the device from the collapsed configuration to the expanded configuration. In some embodiments, the front side 112 and the back side 114 include slots 122 having inwardly facing ramp portions 124 on the outer surfaces proximate the slots 122. The slots 122 and ramp portions 124 can interface with the screw mechanism 106. As shown in FIGS. 3 and 4, the ramp portions 124 slant inward from the bottom toward the top.

In other embodiments not shown, the front side 112 and the back side 114 may include non-ramp features that interface with the screw mechanism 106 to translate inner structure 104 relative to the outer structure 102 from the collapsed configuration to the expanded configuration. For example, as long as the screw mechanism 106 head geometry and the slots 122 or non-ramp features have non-complimentary surfaces, the inner and outer structures may translate and expand. For example, the contact surface of the screw head may be conical or spherical and the outer structure may have a bore with a sharp ledge. As the screw head is drawn toward that ledge, the inner and outer structures may translate and expand.

The inner structure 104 can include a top surface 126, a bottom surface 128, a front side 130, a back side 132, and left and right sides 134. A combination of the sides 130, 132 and 134 forms an outer wall and inner wall that can enclose a central opening 136. The central opening 136 can be configured to receive bone graft material such as allograft and/or Demineralized Bone Matrix ("DBM") packing. In some embodiments, the inner structure 104 may not have a central opening 136 and the top surface 126 can be closed. The inner structure 104 outer wall can be configured to slideably fit within the central opening 118 of the outer structure 102. The front side 130 can include a distal threaded hole 140 and the back side 132 can include a proximal threaded hole 138 that interface with the screw mechanism 106 and are longitudinally aligned with the slots 122 of the outer structure 102. The threaded holes 138, 140 can have threads in opposite directions, one having a left hand thread and the other a right hand thread. With matching opposite threads on the screw mechanism 106, the screw mechanism 106 can contract or extend when turned to expand or collapse the interbody device, as discussed in more detail below. The front side 130, back side 132, left and right sides 134 may have a varying height, length, thickness, and/or curvature radius. In some embodiments, when the inner structure 104 is positioned within the outer structure 102, the height and/or curvature radius of the top surfaces 108, 126, and bottom surfaces, 110, 128, of each should be approximately the same, as shown in FIGS. 1 and 3. In other embodiments, the height and/or curvature radius of each may be different.

The top surfaces 108, 126 and the bottom surfaces 110, 128 of the outer and inner structures 102, 104 can include a plurality of protrusions or teeth 142 (hereinafter, referred to as "teeth"). Teeth 142 can be configured to be spaced throughout the top surfaces 108, 126 and the bottom surfaces 110, 128. As can be understood by one skilled in the art, the teeth 142 can be configured to have variable thickness, height, and width as well as angles of orientation with respect to surfaces 108, 126 and 110, 128. The teeth 142 can be further configured to provide additional support after the expandable interbody device 100 is implanted in the intervertebral space of the patient. The teeth 142 can reduce movement of the outer structure 102 and inner structure 104 with the vertebrae and create additional friction between the vertebrae and the outer structure 102 and inner structure 104.

In some embodiments, the teeth 142 on the top surfaces 108, 126 and the bottom surfaces 110, 128 can be configured to match when the outer structure 102 and inner structure 104 are joined in the collapsed configuration, as shown in FIG. 1. In other embodiments, the teeth 142 on the top surface 108 and the bottom surface 110 of the outer structure 102 may have different spacing, configuration, thickness, height, and width as well as angles of orientation with respect to the teeth 142 on the top surface 126 and the bottom surface 128 of the inner structure 104. In other embodiments, the outer structure 102 and the inner structure 104 may only have the teeth 142 on surfaces that contact the lower and upper vertebrae in the expanded configuration. For example, the outer structure 102 may only have teeth 142 on the bottom surface in contact with the lower vertebrae while the inner structure 104 may only have the teeth 142 on the top surface 126 in contact with the upper vertebrae.

In some embodiments, the top surfaces 108, 126 and the bottom surfaces 110, 128 may be a porous or roughened surface, for example, they may be formed of a porous material, coated with a porous material, or chemically etched to form a porous or roughened surface with pores that participate in the growth of bone with the adjacent vertebra.

As shown in the figures, the screw mechanism 106 can include a proximal section 150 and a distal section 152 loosely coupled in a keyed configuration, such that when the proximal section 150 is rotated, the distal section 152 also rotates as a unit. For example, the distal section 152 may have a keyed shaft outer surface that slideably engages a bore on the proximal section 150 having a matching keyed inner surface. Therefore, the distal section 152 does not have to be rigidly connected to the proximal section 150. One skilled in the art may appreciate that any suitable shapes or geometric configurations for a keyed connection between the proximal and distal sections 150, 152 may be included in the screw mechanism 106 to achieve the desired results.

In use, the screw mechanism 106 engages the outer structure 102 and inner structure 104 such that when it is rotated, the inner structure 104 translates relative to the outer structure 102 from the collapsed configuration to the expanded configuration. If desired, the screw mechanism 106 may be rotated in the opposite direction to translate the inner structure 104 from the expanded configuration back to the collapsed configuration. This allows the expandable interbody device 100 to be moved to another location or repositioned if it is expanded in the wrong location and needs to be collapsed prior to moving or repositioning.

The proximal section 150 and the distal section 152 may be fabricated from any biocompatible material suitable for implantation in the human spine, such as metal including, but not limited to, titanium and its alloys, stainless steel, surgical grade plastics, plastic composites, ceramics, bone, or other suitable materials. In some embodiments, the proximal section 150 and the distal section 152 may be formed of a porous material that participates in the growth of bone with the adjacent vertebral bodies. In some embodiments, the proximal section 150 and the distal section 152 may include a roughened surface that is coated with a porous material, such as a titanium coating, or the material may be chemically etched to form pores that participate in the growth of bone with the adjacent vertebra. In some embodiments, only portions of the proximal section 150 and the distal section 152 may be formed of a porous material, coated with a porous material, or chemically etched to form a porous surface, such as the upper and lower surfaces that contact the adjacent vertebra are roughened or porous. In some embodiments, the surface porosity may be between 50 and 300 microns.

The proximal section 150 can include a shaft 154 with an internal bore 156 extending along its longitudinal axis. In some embodiments, shaft 154 has a cylindrical outer surface and the internal bore has a non-cylindrical surface or keyed surface, such as a square or hexagonal inner surface. The proximal section 150 can also include an external screw threaded portion 158 configured to couple with the proximal threaded hole 138 of the inner structure 104. The proximal end of the shaft can include a proximal circular head 160 adapted to receive a driving tool for rotating or driving the proximal section 150, and the distal end of the shaft 154 can be configured to receive the keyed shaft portion of the distal section 152 within the internal bore 156. Between the external screw thread portion 158 and the head 160 can be a cylindrical engagement portion 162 configured to fit within the slot 122 of the outer structure 102. The distal portion of the head 160 can have a spherical surface 164 configured to engage and slide along the proximal curved or ramp portion 124 of the outer structure 102.

The distal section 152 can include a distal circular head 166, external screw threaded portion 168 configured to couple with the distal threaded hole 140 of the inner structure 104, a cylindrical engagement portion 162 positioned between the distal head 166 and external screw thread portion 168 configured to fit within the distal slot 122 of the outer structure 102, and a keyed shaft 170 portion. The keyed shaft 170 portion can be configured to slideably fit within the internal bore 156 of the proximal section 150. When joined, the keyed shaft 170 portion and internal bore 156 act as a keyed shaft and sleeve arrangement, such that when the proximal section 150 is rotated, the distal section 152 also rotates as a unit. The proximal portion of the head 166 can have a spherical surface 172 configured to engage and slide along the distal curved or ramp portion 124 of the outer structure 102, as illustrated in FIGS. 3 and 4.

As mentioned above, the external screw threaded portions 158, 168 of the screw mechanism 106 can match the threaded holes 138, 140 of the inner structure 104. Since threaded holes 138, 140 have thread patterns in opposite directions, the external screw thread portions 158, 168 may also have matching thread patterns in opposite directions. In some embodiments, the threaded holes and external screw thread portions may have equal pitch, such that during expansion, the proximal and distal end of the outer structure 102 and inner structure 104 translate or move at the same rate. In other embodiments, the proximal threaded hole and proximal external screw thread portion may have a different pitch than the distal threaded hole and distal external screw thread portion, such that during expansion, the proximal and distal ends of the outer structure 102 and inner structure 104 translate or move at different rates. For example, the proximal end of the outer structure 102 and inner structure 104 may translate or move at a first rate of speed and the distal end of the outer structure 102 and inner structure 104 may translate or move at a second rate of speed. The first rate of speed may be faster or slower than the second rate of speed. This allows for some angularity between the outer structure 102 and inner structure 104 during expansion. The difference between the first and second rates of speed allows the user to select an expandable interbody device 100 that has some angulation after expansion to account for the lordotic curvature of the spine.

When the screw mechanism 106 is coupled to the inner structure 104 it may vary in length during interbody expansion (as shown in FIGS. 3 and 4). Initially, the length of the screw mechanism 106 can be L1 in the collapsed configuration, shown in FIG. 3. As the screw mechanism 106 is rotated in a first direction, it acts like a compression screw and the length of the screw mechanism 106 contracts to L2 in the expanded configuration, shown in FIG. 4, due to the threads on the proximal and distal sections being threaded in opposite directions. By reversing rotation of the screw mechanism 106 in a second direction, opposite the first, the screw mechanism 106 may extend in length from L2 back to L1, if desired.

Figure 5:
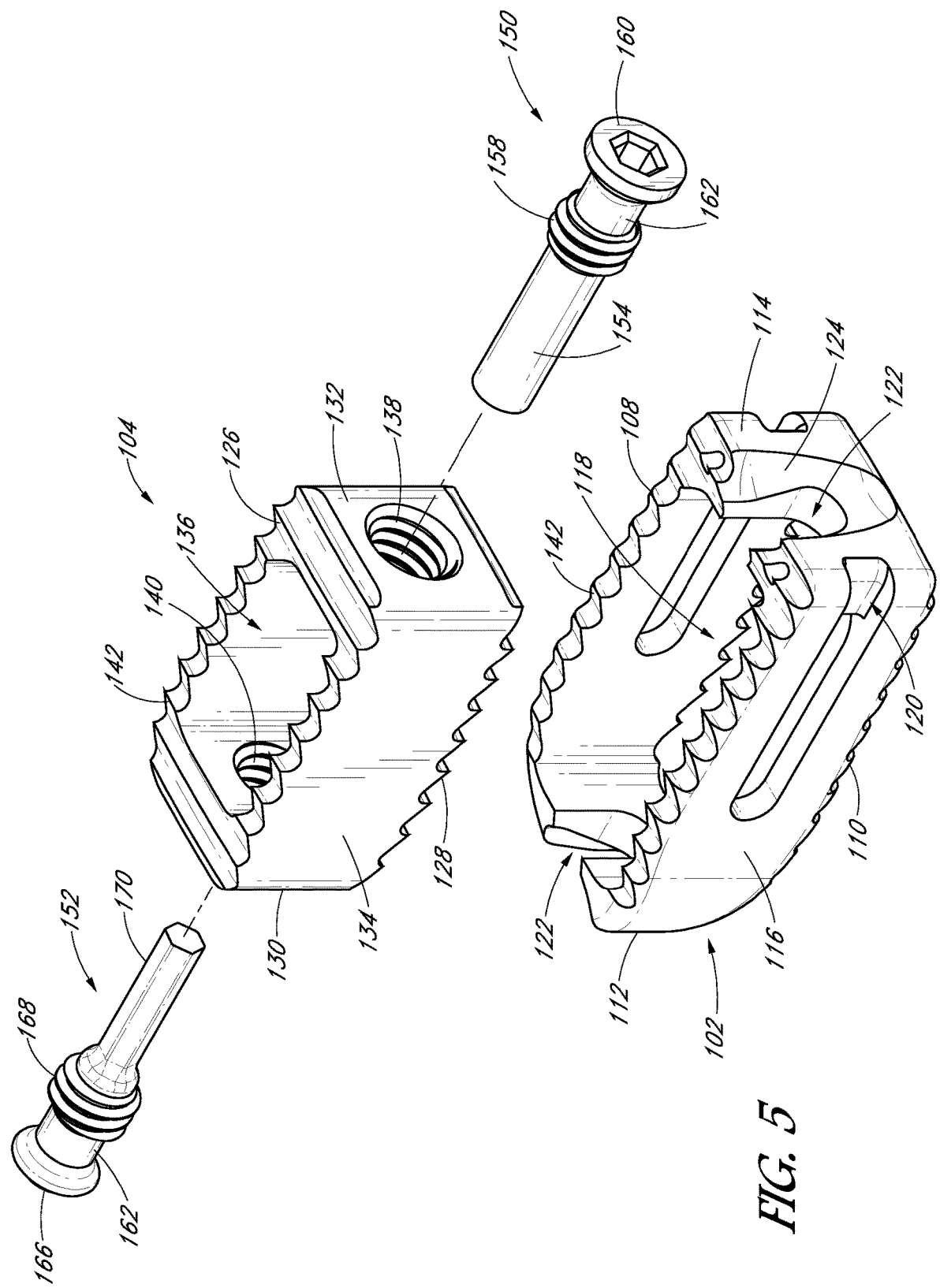
FIG. 5 is a perspective exploded view showing the expandable interbody device of FIG. 1, including the outer structure, inner structure and screw mechanism.
Figure 6:
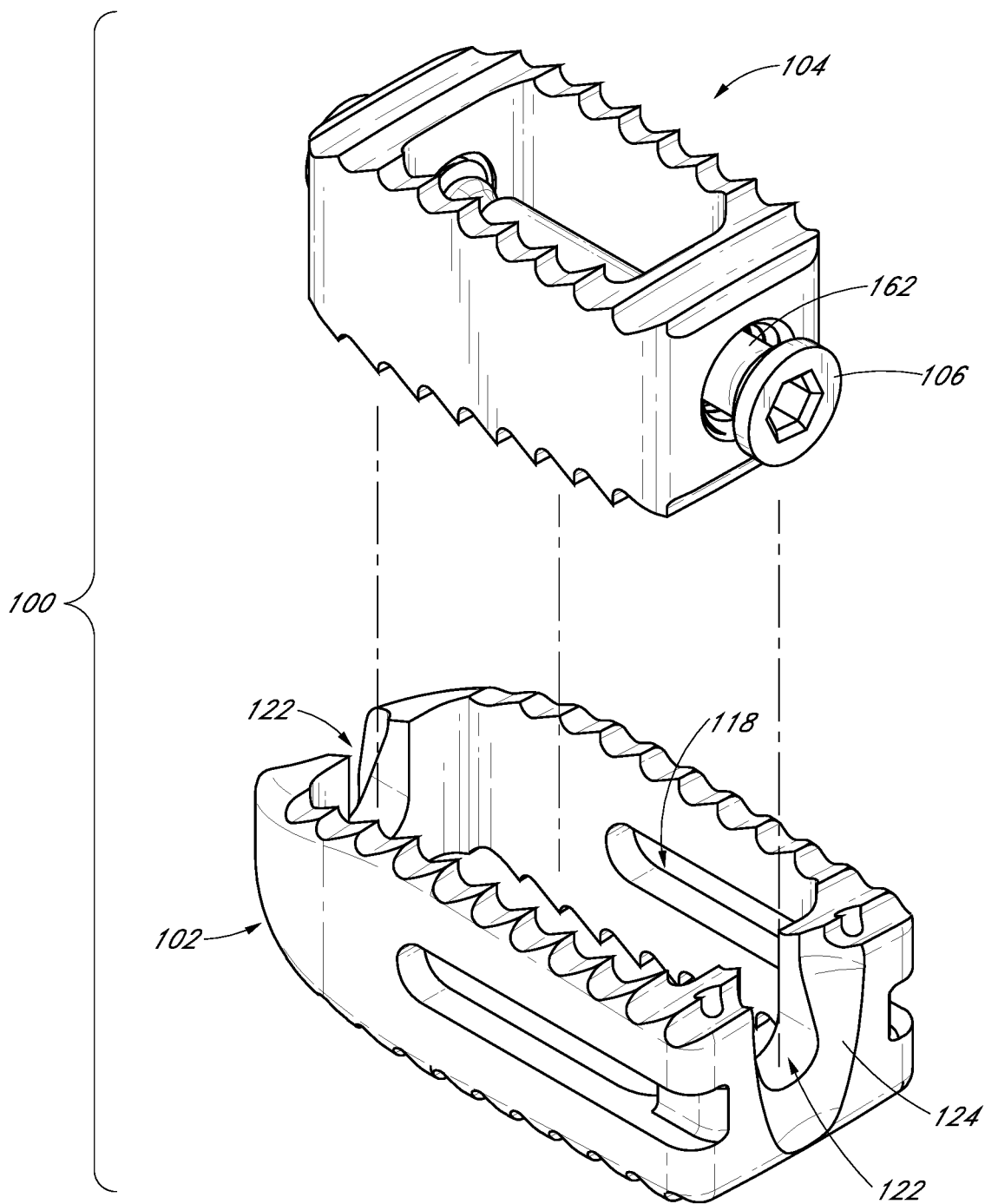
FIG. 6 is a perspective exploded view showing the expandable interbody device of FIG. 1 with the screw mechanism assembled with the inner structure prior to assembly into the outer structure.

Referring to FIGS. 5 and 6, the expandable interbody device 100 can be assembled by inserting the proximal section 150 of the screw mechanism 106 into proximal threaded hole 138 and the distal section 152 of the screw mechanism 106 into distal threaded hole 140. The external screw threaded portions 158, 168 engage the threaded holes 138, 140 and the keyed shaft 170 of the distal section 152 is slid within and engaged, or keyed, with the internal bore 156 of the proximal section 150. The screw mechanism 106 is then rotated in the direction for contraction until the engagement portion 162 for each section is left exposed (see FIG. 6). The inner structure 104 may then be lowered into the central opening 118 of the outer structure 102, with the engagement portions 162 sliding into the proximal and distal slots 122 of the outer structure 102. The screw mechanism 106 is then rotated until the spherical surface 164 of the proximal head 158 and the spherical surface 172 of the distal head 168 engage the proximal and distal curved or ramp portions 124 of the outer structure 102, shown in FIG. 3. The expandable interbody device 100 is now ready to be inserted.

Referring back to FIGS. 3 and 4, in the collapsed configuration the expandable interbody device 100 may have a height of H1. The proximal head 160 spherical surface 164 is engaged with the proximal ramp portion 124 of the outer structure 102 and the distal head 166 spherical surface 172 is engaged with the distal ramp portion 124 of the outer structure 102. When the screw mechanism 106 is rotated in a first direction, the proximal head 160 and the distal head 166 can move toward each other (from L1 to L2). While this happens, the spherical surfaces 164 and 172 start sliding up the proximal and distal incline ramps 124 and translating the inner structure 104 vertically from H1 (collapsed configuration) toward H2 (expanded configuration). The expandable interbody device 100 does not have to be completely extended to H2 and can be stopped anywhere between H1 and H2, depending on the expansion needed between the adjacent vertebrae. The proximal and distal ramps 124 may also have features that that require more force or less force on the screw mechanism 106 during expansion. This difference in forces may provide tactile feedback to the surgeon as an indication of expansion of the expandable interbody device 100.

In some embodiments, the screw mechanism may be a compression screw having a proximal section threadably coupled to a distal section, the proximal section having a threaded shaft and the distal section having a threaded bore, such that when the proximal section is rotated, the threaded shaft engages the threaded bore to shorten or lengthen the distance between the proximal head 158 and the distal head 168. In this embodiment, holes 138, 140 would be sized to slideably fit the proximal and distal shafts of the compression screw and would not be threaded holes.

The expandable interbody device 100 may also include a deployment tool. The deployment tool may include various attachment features to enable insertion of the expandable interbody device 100 into the patient. For example, the deployment tool may include arms or clamps to attach to the longitudinal openings, slots or trenches 120 of the outer structure 102 and an actuation device to couple with the head 160 of the proximal section 150 of the screw mechanism 106. Once the expandable interbody device 100 has been inserted and positioned within the intervertebral space between two vertebrae, the deployment tool may actuate to deploy and expand the expandable interbody device 100 by applying a rotational force to screw mechanism 106.

In operation, the expandable interbody device 100 may be inserted into the intervertebral disc space between two vertebrae using an insertion or deployment tool. In some cases, the disc space may include a degenerated disc or other disorder that may require a partial or complete discectomy prior to insertion of the expandable interbody device 100. The deployment tool may engage with the proximal end of the expandable interbody device 100. As the deployment tool applies the rotational force, the expandable interbody device 100 gradually expands as described above. The deployment tool may allow an increase in the amount of force that can be applied to the screw mechanism 106 to overcome the friction or interference between the spherical surfaces 164, 172 of the distal and proximal heads and ramp portions of the outer structure 104 during expansion of the expandable interbody device 100. The increase in the force may be used to provide tactile feedback to the surgeon indicating near complete deployment of the expandable interbody device 100.

In some embodiments, more than one expandable interbody device 100 can be implanted between the adjacent vertebrae of the patient. In such embodiments, multiple expandable interbody devices 100 can be placed in a side-by-side configuration or any other suitable configuration, thereby creating additional support.

Referring now to FIGS. 7-11, an expandable interbody device 200 can be a spinal implant that includes an outer structure 202, an inner structure 204, and a screw mechanism 206. The expandable interbody device 200 can be movable between a collapsed configuration (show in FIG. 7) to an expanded configuration (shown in FIG. 8) utilizing the screw mechanism 206.

Figure 10:
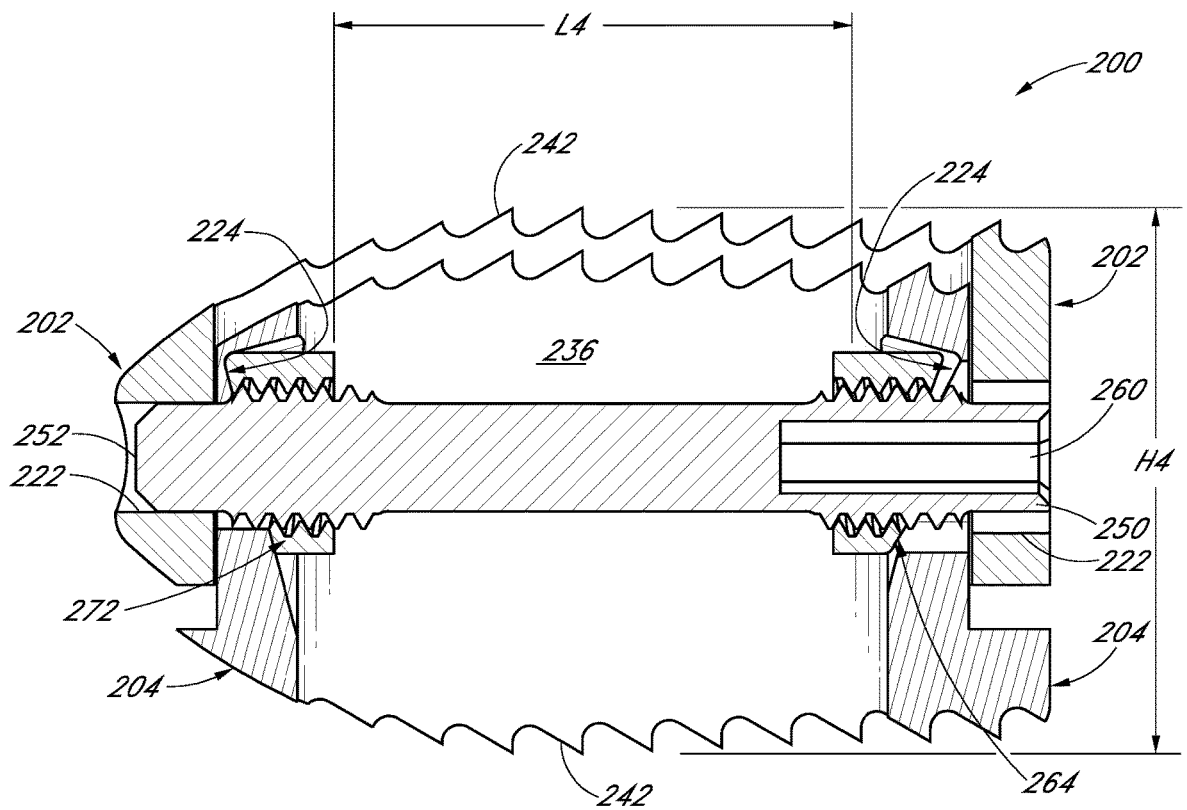
FIG. 10 is a cross-sectional view of the expandable interbody device of FIG. 8 in an expanded configuration.
Figure 11:
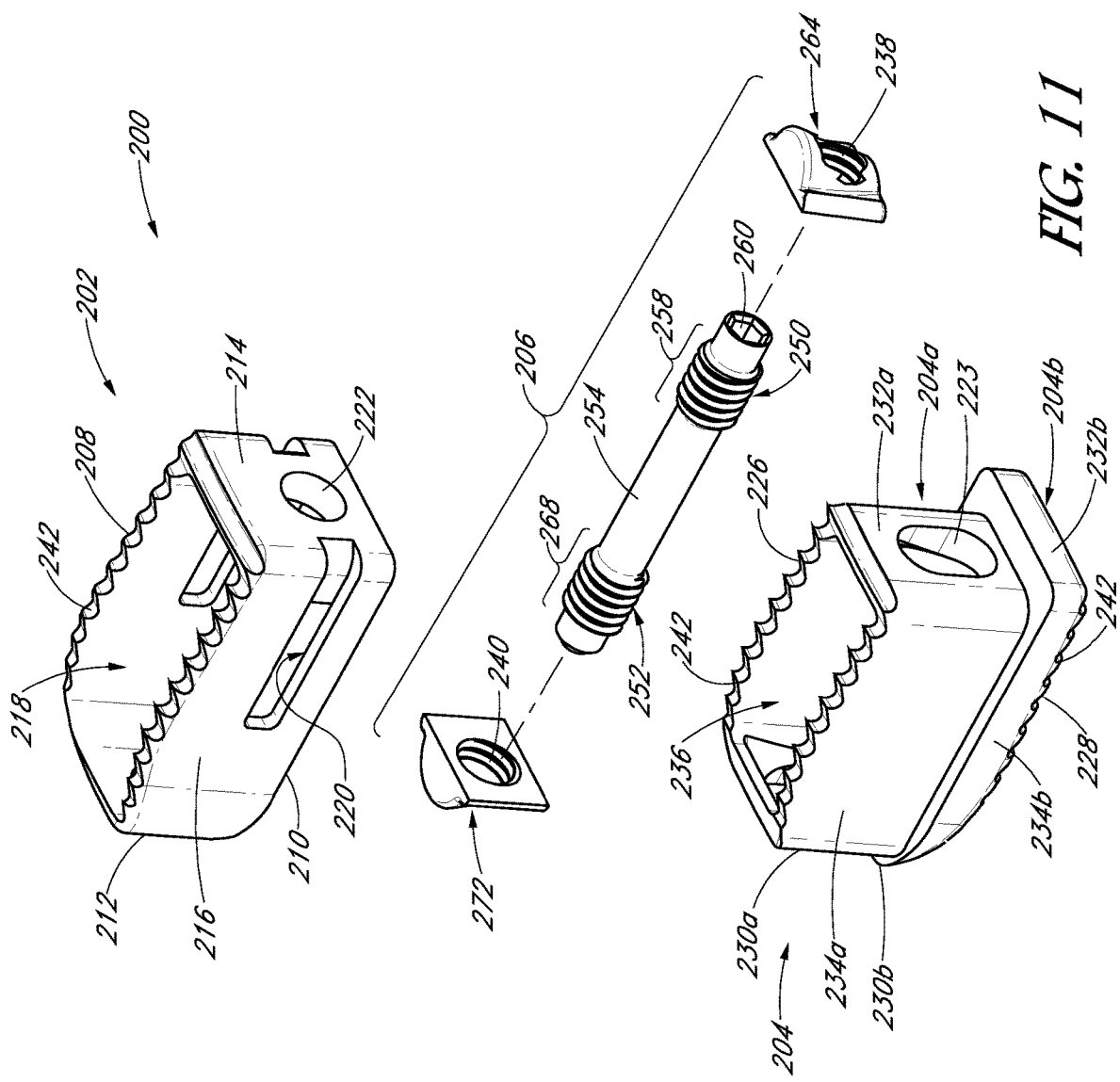
FIG. 11 is a perspective exploded view showing the expandable interbody device of FIG. 7, including the outer structure, inner structure and screw mechanism.

Referring now to FIG. 11, the outer structure 202 can include a top surface 208, a bottom surface 210, a front side 212, a back side 214, and left and right sides 216. A combination of the sides 212, 214 and 216 can form a wall that encloses a central opening 218. The front side 212, back side 214, left and right sides 216 may have a varying height, length, thickness, and/or curvature radius. The left and right sides 216 may include longitudinal openings, slots or trenches 220 configured to interface with an insertion and/or deployment tool (not shown) during implantation and deployment of the device from the collapsed configuration to the expanded configuration. The front side 212 and the back side 214 can have holes 222 sized to slideably fit portions of the screw mechanism 206, see FIGS. 9 and 10.

The inner structure 204 can include an inner portion 204a and a lower flanged portion 204b. The inner portion 204a can include a top surface 226, a front side 230a, a back side 232a, and left and right sides 234a. In the illustrated embodiment, a combination of the sides 230a, 232a and 234a forms an outer wall and inner wall that encloses a central opening 236. The inner portion 204a outer wall can be configured to slideably fit within the central opening 218 of the outer structure 202, as shown in the figures. The front side 230a and the back side 232a can include slots 223 sized to slideably fit the screw mechanism 206 threads. The holes 222 of the outer structure 202 are aligned with the slots 223.

The lower flanged portion 204b of the inner structure 204 can include a bottom surface 228, a front side 230b, a back side 232*b*, and left and right sides 234*b*. A combination of the sides 230*b*, 232*b* and 234*b* forms an outer wall and inner wall. The inner wall of the lower flanged portion 204*b* can also enclose the central opening 236.

Figure 9:
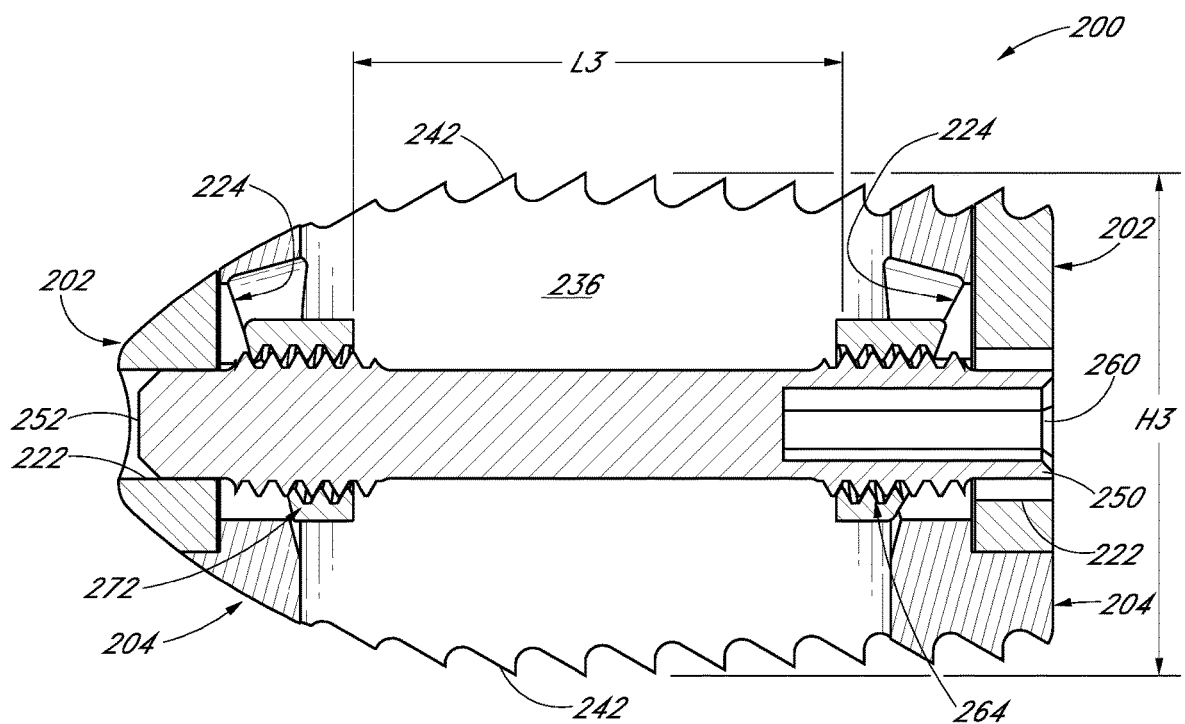
FIG. 9 is a cross-sectional view of the expandable interbody device of FIG. 7 in a collapsed configuration.

On the inner wall of the front side 230*a* and back side 232*a* are inwardly facing ramps 224 proximate the slots 223 within the central opening 236 of the inner structure 204 that interface with the screw mechanism 206, shown in FIGS. 9 and 10.

Figure 7:
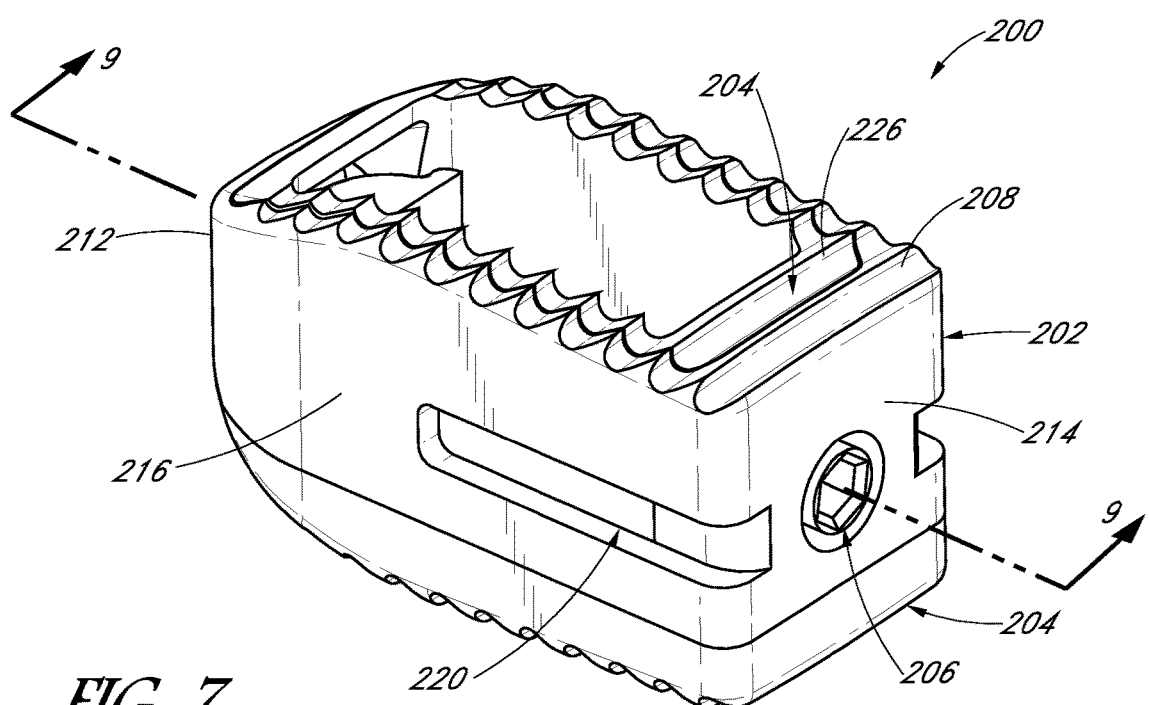
FIG. 7 is a perspective view showing an expandable interbody device in a collapsed configuration, according to another embodiment of the present invention.
Figure 8:
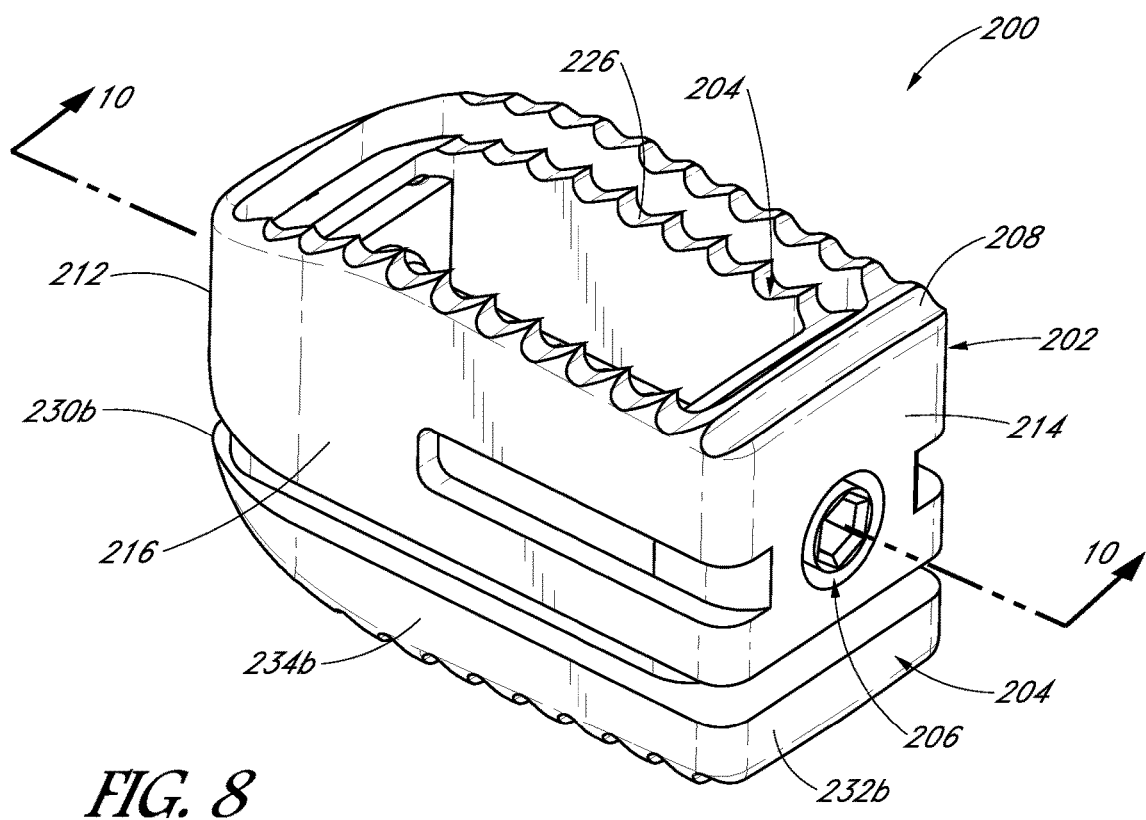
FIG. 8 is a perspective view showing the expandable interbody device of FIG. 7 in an expanded configuration.

The front sides 230*a*, 230*b*, back sides 232*a*, 232*b*, left and right sides 234*a*, 234*b*, may have a varying height, length, thickness, and/or curvature radius. In some embodiments, when the inner structure 204 is positioned within the outer structure 202, the curvature radius of the top surfaces 208, 226 can be approximately the same, as shown in FIGS. 7 and 9. In other embodiments, the curvature radius of each may be different. In some embodiments, the outer wall of the lower flanged portion 204*b* is approximately the same shape as the outer wall of the outer structure 202, as shown in FIGS. 7 and 9. In other embodiments, the outer wall of each may be different. The central opening 236 can be configured to receive bone graft material such as allograft and/or Demineralized Bone Matrix ("DBM") packing.

The top surfaces 208, 226 and the bottom surface 228 of the outer and inner structures 202, 204 can include a plurality of protrusions or teeth 242 (hereinafter, referred to as "teeth"). Teeth 242 can be configured to be spaced throughout the top surfaces 208, 226 and the bottom surface 228. As can be understood by one skilled in the art, the teeth 242 can be configured to have variable thickness, height, and width as well as angles of orientation with respect to surfaces 208, 226 and 228. The teeth 242 can be further configured to provide additional support after the expandable interbody device 200 is implanted in the intervertebral space of the patient. The teeth 242 can reduce movement of the outer structure 202 and inner structure 204 with the vertebrae and create additional friction between the vertebrae and the outer structure 202 and inner structure 204.

In some embodiments, the teeth 242 on the top surfaces 208, 226 can be configured to match when the outer structure 202 and inner structure 204 are joined in the collapsed configuration, as shown in FIG. 7. In other embodiments, the teeth 242 on the top surface 208 of the outer structure 202 may have different spacing, configuration, thickness, height, and width as well as angles of orientation with respect to the teeth 242 on the top surface 226 of the inner structure 204. In other embodiments, the outer structure 202 and the inner structure 204 may only have the teeth 242 on surfaces that contact the lower and upper vertebrae in the expanded configuration. For example, the outer structure 202 may only have teeth 242 on the top surface 208 in contact with the first vertebrae while the inner structure 204 may only have the teeth 242 on the bottom surface 228 in contact with the second vertebrae.

In some embodiments, the top surfaces 208, 226 and the bottom surface 228 may be a porous or roughened surface, for example, they may be formed of a porous material, coated with a porous material, or chemically etched to form a porous or roughened surface with pores that participate in the growth of bone with the adjacent vertebra.

The proximal section 250 and the distal section 252 of the screw mechanism 206 may be fabricated from any biocompatible material suitable for implantation in the human spine, such as metal including, but not limited to, titanium and its alloys, stainless steel, surgical grade plastics, plastic composites, ceramics, bone, or other suitable materials. In some embodiments, the proximal section 250 and the distal section 252 may be formed of a porous material that participates in the growth of bone with the adjacent vertebral bodies. In some embodiments, the proximal section 250 and the distal section 252 may include a roughened surface that is coated with a porous material, such as a titanium coating, or the material is chemically etched to form pores that participate in the growth of bone with the adjacent vertebra. In some embodiments, only portions of the proximal section 250 and the distal section 252 may be formed of a porous material, coated with a porous material, or chemically etched to form a porous surface, such as the upper and lower surfaces that contact the adjacent vertebra are roughened or porous. In some embodiments, the surface porosity may be between 50 and 300 microns.

As shown in the figures, the screw mechanism 206 can include a shaft 254, a proximal ramped component 264 and a distal ramped component 272. The proximal end of the shaft can include an opening 260 adapted to receive a driving tool for rotating the shaft 254. The proximal and distal ramped components 264, 272 can have threaded holes 238, 240 with threads in opposite directions, hole 238 having a left hand thread and hole 240 a right hand thread, or vice versa. In the illustrated embodiment, the shaft 254 includes proximal section 250 with external threads 258, and distal section 252 with external threads 268 in opposite directions, external threads 258 having a left hand thread and external thread 268 having a right hand thread, or vice versa, matching the threads 238, 240 of the proximal and distal ramped components 264, 272. When assembled, proximal ramped component 264 is threaded onto the proximal thread 258 of the proximal section 250 while the distal ramped component 272 is threaded onto the distal thread 268 of the distal section 252. Having opposite threads on the proximal and distal ramped components 264, 272 matching the proximal and distal sections 250, 252 can allow the proximal and distal ramped components 264, 272 to extend or contract along the shaft 254 when the screw mechanism 206 is rotated or turned to expand or collapse the interbody device (see below).

In use, the proximal and distal ramped components 264, 272 of the screw mechanism 206 can engage the inwardly facing ramps 224 and the proximal and distal sections 250, 252 can extend through slots 223 of the inner structure 204 and into holes 222 of the outer structure 202 (shown in FIGS. 9 and 10). When the screw mechanism 206 is rotated, the proximal and distal ramped components 264, 272 move along the shaft 254 and slide along the inwardly facing ramps 224 of the inner structure 204 and the proximal and distal sections 250, 252 slide in slots 223 of the inner structure 204, while the extreme part of the proximal and distal sections 250, 252 stay within the holes 222 of the outer structure 202. This action translates the inner structure 204 relative to the outer structure 202 from the collapsed configuration to the expanded configuration. If desired, the screw mechanism 206 may be rotated in the opposite direction to translate the inner structure 204 from the expanded configuration back to the collapsed configuration. This can allow the expandable interbody device 200 to be moved to another location or reposition if it is expanded in the wrong location and needs to be collapsed prior to moving or repositioning. The shaft 254, the proximal and distal ramped components 264, 272, the outer structure 202 and inner structure 204 may be fabricated from any biocompatible material such as stainless steel, or other suitable material.

As discussed above, the external screw threaded portions 258, 268 can match the threaded holes 238, 240 of the ramped components 264, 272. Since threaded holes 238, 240 may have thread patterns in opposite directions, the external screw thread portions 258, 268 may also have matching thread patterns in opposite directions. In some embodiments, the threaded holes and external screw thread portions may have equal pitch, such that during expansion, the proximal and distal end of the outer structure 202 and inner structure 204 translate or move at the same rate. In other embodiments, the proximal threaded hole and proximal external screw thread portion may have a different pitch than the distal threaded hole and distal external screw thread portion, such that during expansion, the proximal and distal ends of the outer structure 202 and inner structure 204 translate or move at different rates. For example, the proximal end of the outer structure 202 and inner structure 204 may translate or move at a first rate of speed and the distal end of the outer structure 202 and inner structure 204 may translate or move at a second rate of speed. The first rate of speed may be faster or slower than the second rate of speed. This can allow for some angularity between the outer structure 202 and inner structure 204 during expansion. The difference between the first and second rates of speed can allow the user to select an expandable interbody device 200 that has some angulation after expansion to account for the lordotic curvature of the spine.

When the screw mechanism 206 is coupled to the inner structure 204 the distance between the ramped components 264, 272 can vary in length during interbody expansion (as shown in FIGS. 9 and 10). Initially, the distance is L3 in the collapsed configuration, shown in FIG. 9. As the screw mechanism 206 is rotated in a first direction, the distance between the ramped components 264, 272 can extend in length to L4 in the expanded configuration, shown in FIG. 10, due to the threads on the proximal and distal sections and ramped components being threaded in opposite directions. By reversing rotation of the screw mechanism 206 in a second direction, opposite the first, the distance may shorten in length from L4 back to L3, if desired.

Referring back to FIGS. 9 and 10, in the collapsed configuration the expandable interbody device 200 can have a height of H3. The proximal ramped component 264 can be engaged with the proximal ramp portion 224 and the distal ramped component 272 can be engaged with the distal ramp portion 224 of the inner structure 204. When the screw mechanism 206 is rotated in a first direction, the proximal ramped component 264 and the distal ramped component 272 can move away from each other (from L3 to L4). While this happens, the proximal and distal ramped components 264 and 272 are forced against the proximal and distal incline ramps 224, sliding the proximal and distal incline ramps 224 in a downward direction, translating the inner structure 204 vertically downward from H3 (collapsed configuration) toward H4 (expanded configuration). The expandable interbody device 200 does not have to be completely extended to H4 and can be stopped anywhere between H3 and H4, depending on the expansion needed between the adjacent vertebrae. The proximal and distal ramps 224 may also have features that that require more force or less force on the screw mechanism 206 during expansion. This difference in forces may provide tactile feedback to the surgeon as an indication of expansion of the expandable interbody device 200.

The expandable interbody device 200 may also include a deployment tool. The deployment tool may include various attachment features to enable insertion of the expandable interbody device 200 into the patient. For example, the deployment tool may include arms or clamps to attach to the longitudinal openings, slots or trenches 220 of the outer structure 202 and an actuation device to couple with the head 260 of the proximal section 250 of the screw mechanism 206. Once the expandable interbody device 200 has been inserted and positioned within the intervertebral space between two vertebrae, the deployment tool may actuate to deploy and expand the expandable interbody device 200 by applying a rotational force to screw mechanism 206.

In operation, the expandable interbody device 200 may be inserted into the intervertebral disc space between two vertebrae using an insertion or deployment tool. In some cases, the disc space may include a degenerated disc or other disorder that may require a partial or complete discectomy prior to insertion of the expandable interbody device 200. The deployment tool may engage with the proximal end of the expandable interbody device 200. As the deployment tool applies the rotational force, the expandable interbody device 200 can gradually expand as described above. The deployment tool may allow an increase in the amount of force that can be applied to the screw mechanism 206 to overcome the friction or interference between the proximal and distal ramped components 264, 272 and ramp portions 224 of the inner structure 204. The increase in the force may be used to provide tactile feedback to the surgeon indicating near complete deployment of the expandable interbody device 200.

In some embodiments, more than one expandable interbody device 200 can be implanted between the adjacent vertebrae of the patient. In such embodiments, multiple expandable interbody devices 200 can be placed in a side-by-side configuration or any other suitable configuration, thereby creating additional support.

Figure 12:
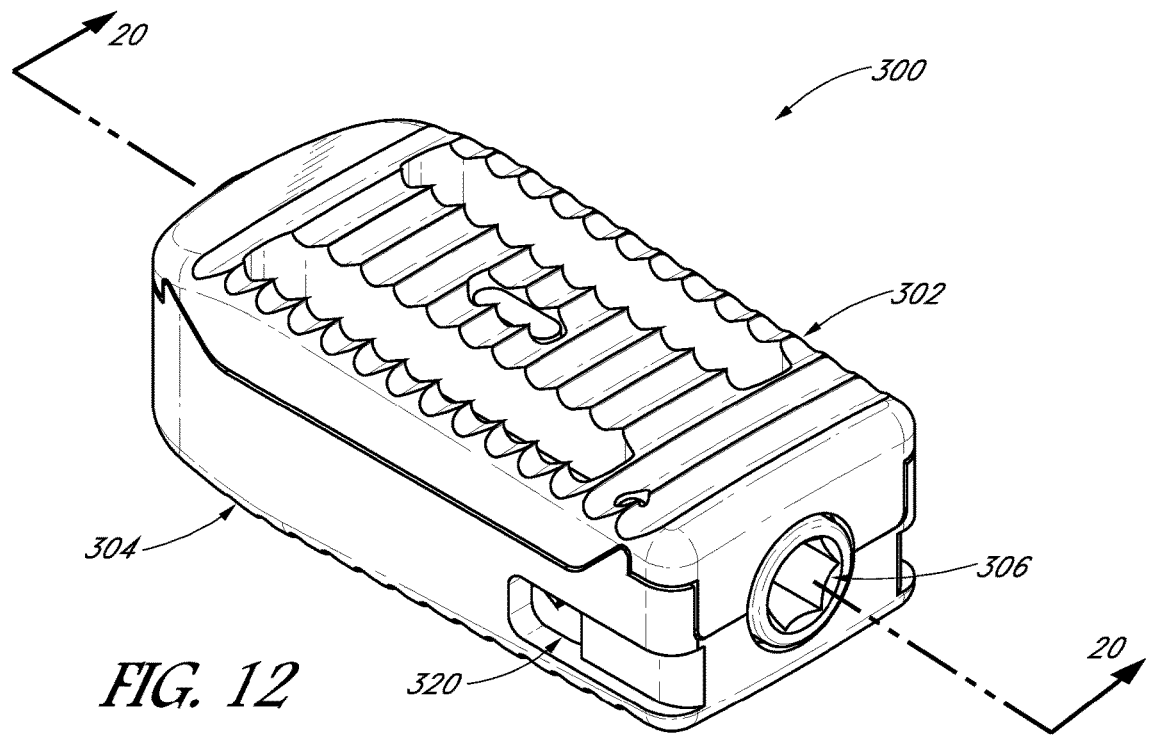
FIG. 12 is a perspective view showing an expandable interbody device in a collapsed configuration, according to another embodiment of the present invention.
Figure 13:
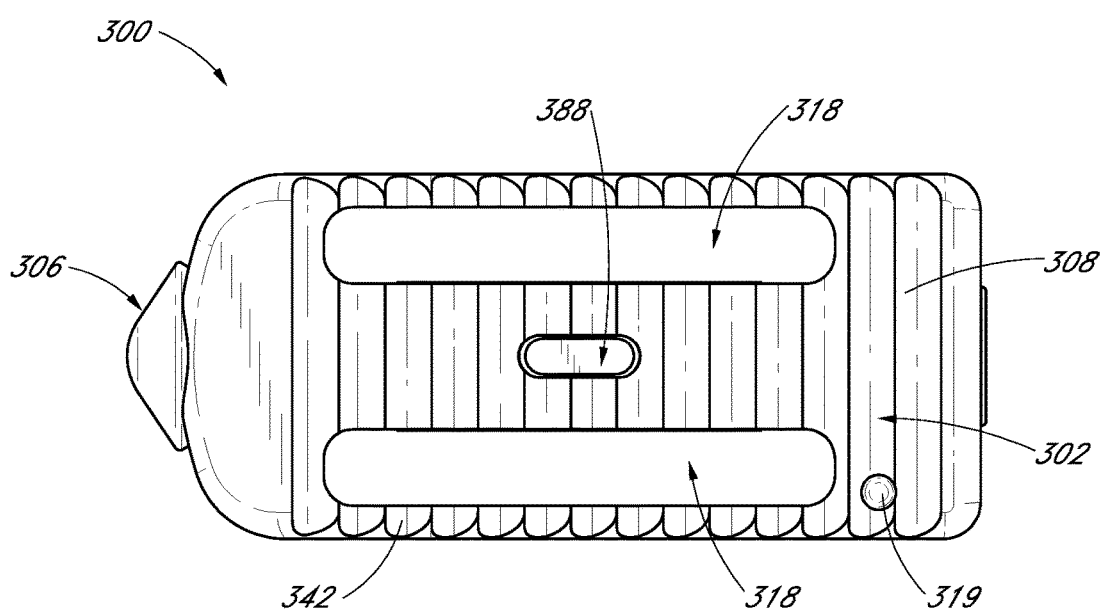
FIG. 13 is a top view of the expandable interbody device of FIG. 12.
Figure 14:
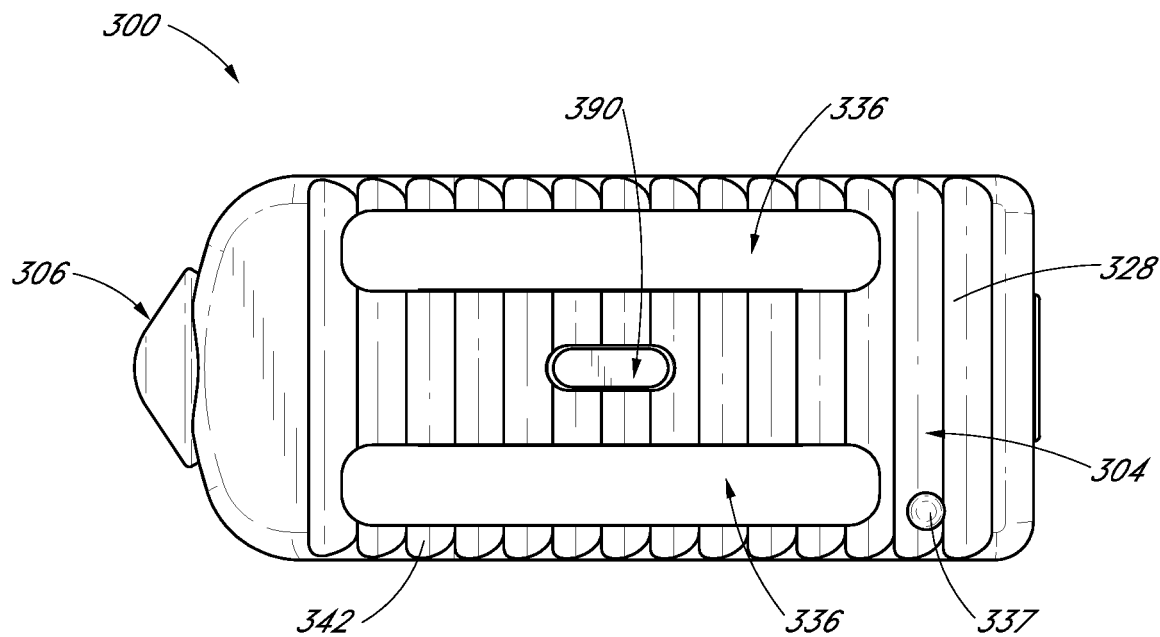
FIG. 14 is a bottom view of the expandable interbody device of FIG. 12.
Figure 18:
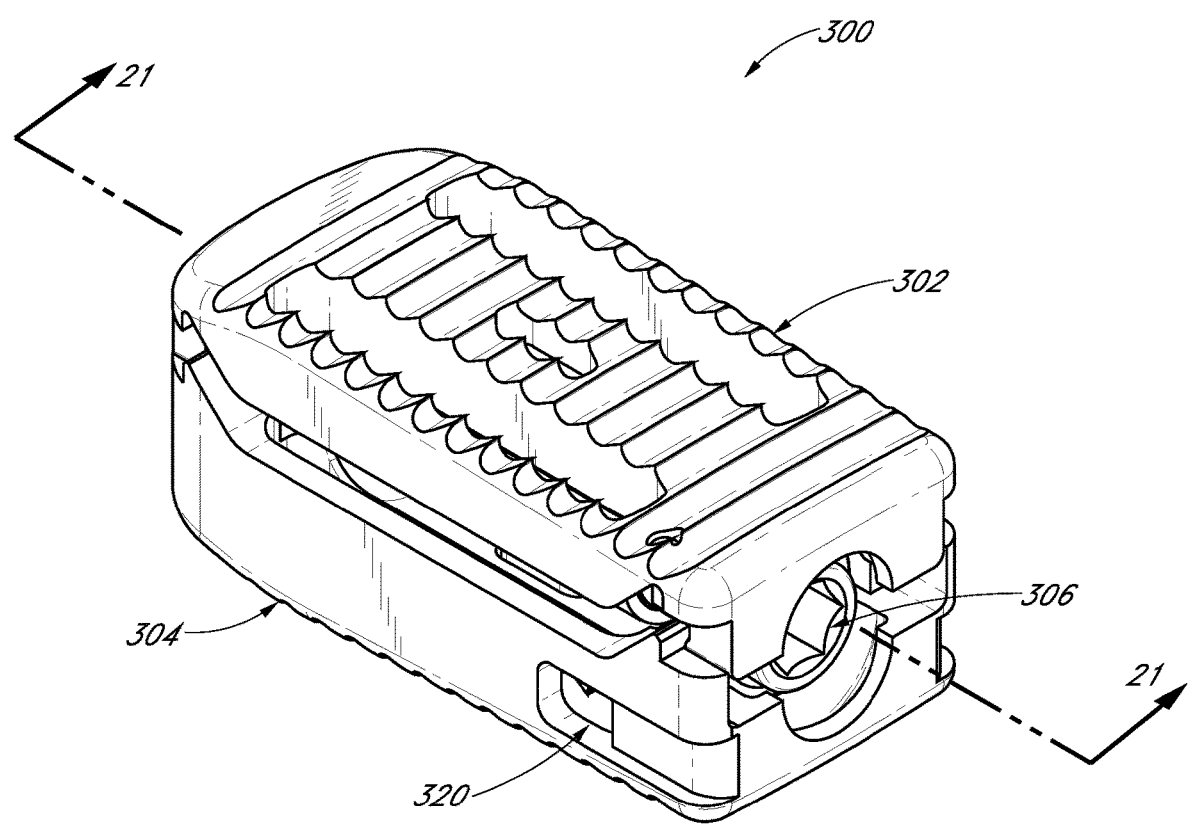
FIG. 18 is a perspective view showing the expandable interbody device of FIG. 12 in an expanded configuration.

With reference to FIGS. 12-19, some embodiments of the expandable interbody device 300 can include an upper structure 302, a lower structure 304, and a screw mechanism 306. The expandable interbody device 300 can be changeable between a collapsed configuration, as shown in FIG. 12, to an expanded configuration, as shown in FIG. 18.

The upper structure 302 can include a top surface 308, a distal side 312, a proximal side 314, and left and right sides 316. One or more slots 318 can extend through the upper structure 302, having an opening on the top surface 308 that is in fluid communication with the bottom of the upper structure 302. The one or more slots 318 can be configured to receive fluids, medication, bone graft material, or other material to help in the integration of the interbody device with the vertebrae, such as with allograft and/or Demineralized Bone Matrix ("DBM") packing. The distal side 312, proximal side 314, and left and right sides 316 may have a varying height, length, thickness, and/or curvature radius. In some embodiments, the upper structure 302 may not have any slots and the top surface 308 can be closed. In some embodiments, the upper structure 302 can have one or more markers 319 to help visualization using radiation during the implantation procedure. The marker 319 can be made of a radiopaque material, such as titanium.

The lower structure 304 can include a bottom surface 328, a distal side 330, a proximal side 332, and left and right sides 334. One or more slots 336 can extend through the lower structure 304, having an opening on the bottom surface 328 that is in fluid communication with the top of the lower structure 304. In some embodiments, the one or more slots 336 may line up with the one or more slots 318 on the upper structure 302, such that the slots extend through the interbody device 300. The one or more slots 336 can be configured to receive fluids, medication or other material to help in the integration of the interbody device with the vertebrae, such as with allograft and/or Demineralized Bone Matrix ("DBM") packing. The distal side 330, proximal side 332, and left and right sides 334 may have a varying height, length, thickness, and/or curvature radius. In some embodiments, the lower structure 304 may not have any slots and the bottom surface 328 can be closed. In some embodiments, the lower structure 304 can have one or more markers 337 to help visualization using radiation during the implantation procedure. The marker 337 can be made of a radiopaque material, such as titanium. The left and right sides 334 may include recesses 320 configured to interface with a deployment tool during implantation and deployment of the device from the collapsed configuration to the expanded configuration, as explained below. In some embodiments, the recesses 320 can extend through to the inner cavity of the interbody device and can be used as an access location for delivering fluids, medication or other material, as discussed below.

Figure 15:
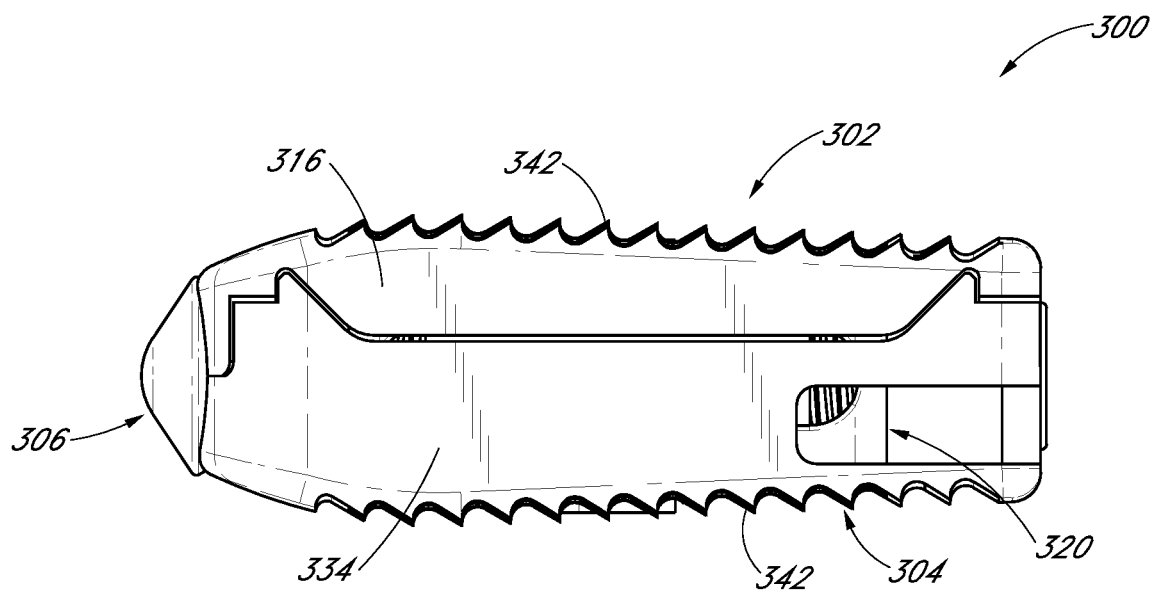
FIG. 15 is a side view of the expandable interbody device of FIG. 12.
Figure 16:
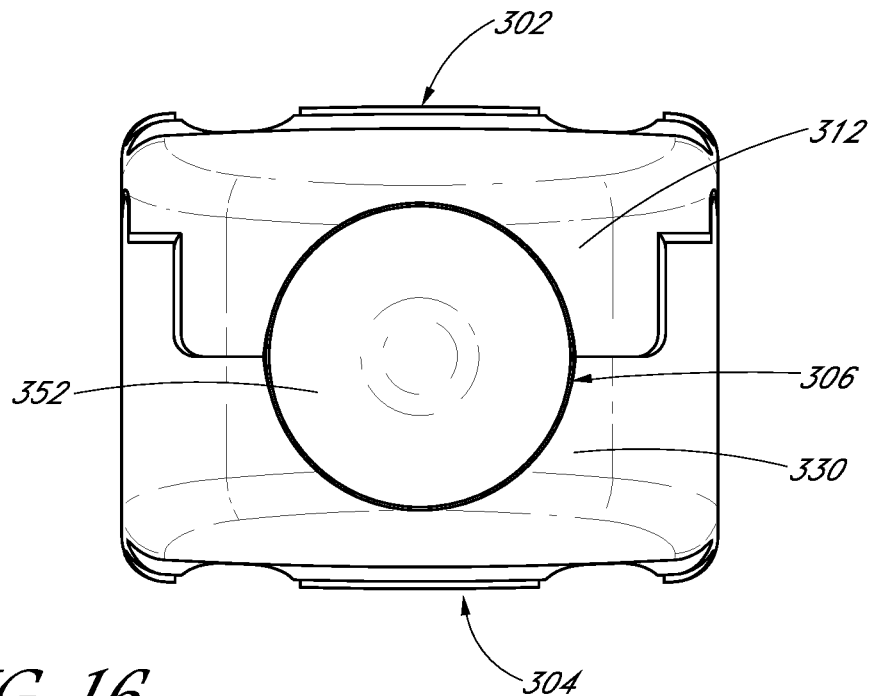
FIG. 16 is a front view of the expandable interbody device of FIG. 12.
Figure 17:
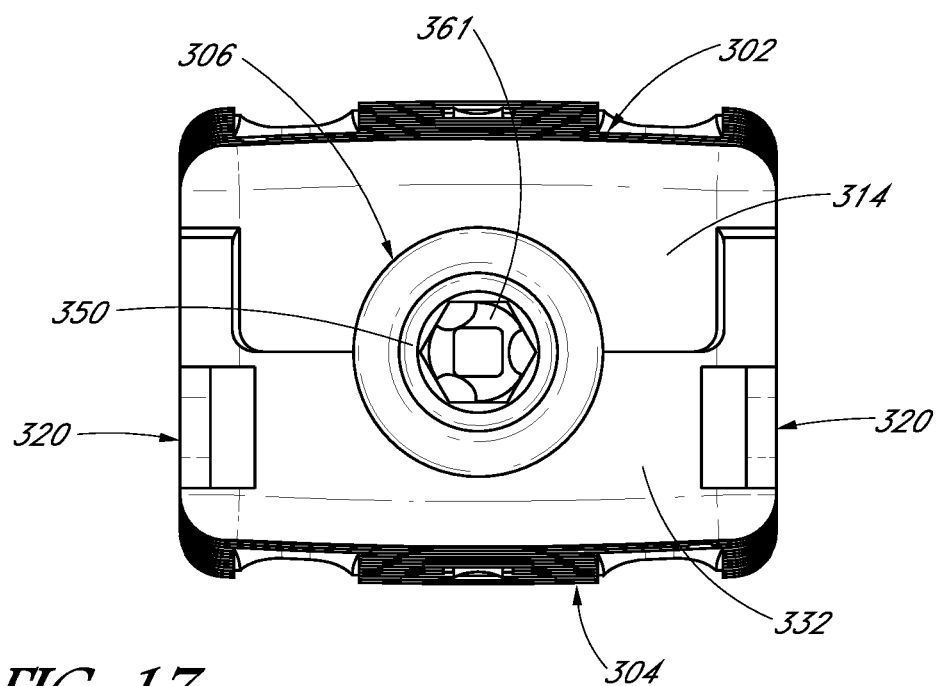
FIG. 17 is a rear view of the expandable interbody device of FIG. 12.

The top surface 308 of the upper structure 302 and the bottom surface 328 of the lower structure 304 can have a roughened surface, such as a plurality of protrusions or teeth 342. The protrusions can be configured to be spaced throughout the top surface 308 and the bottom surface 328. As can be understood by one skilled in the art, the protrusions can be configured to have variable thickness, height, and width as well as angled surfaces. For example, as illustrated in FIG. 15, the top surface 308 and bottom surface 328 can have teeth 342 that are angled toward the proximal side. The distal facing side of the teeth 342 are less steep than the proximal facing side of the teeth 342. This can allow for easy insertion of the interbody device and help prevent backing out of the device from the intervertebral space. The teeth 342 can be configured to provide additional support after the expandable interbody device 300 is implanted in the intervertebral space of the patient. For example, the friction between the vertebrae and the upper structure 302 and lower structure 304, provided at least in part by the teeth 342, can help reduce movement of the interbody device 300 in the intervertebral space.

The upper structure 302 and lower structure 304, or portions thereof, can be made of any of a variety of materials known in the art, including but not limited to a polymer such as polyetheretherketone (PEEK), polyetherketoneketone (PEKK), polyethylene, fluoropolymer, hydrogel, or elastomer; a ceramic such as zirconia, alumina, or silicon nitride; a metal such as titanium, titanium alloy, cobalt chromium or stainless steel; or any combination of the above materials. The interbody device 300 may be made of multiple materials in combination. For example, the upper structure 302 can comprise a polymer, such as PEEK or polyethylene, and the lower structure 304 can comprise a metal or ceramic.

In some embodiments, the upper structure 302 and/or the lower structure 304 may be formed of a porous material or have a roughened surface. The surfaces may be formed of a porous material, coated with a porous material, or chemically etched to form a porous or roughened surface with pores, which may help participate in the growth of bone with the adjacent vertebra. In some embodiments, only portions of the interbody device 300 may be formed of a porous material, coated with a porous material, or chemically etched to form a porous surface. For example, at least some portions of the top surface 308 and/or the bottom surface 328 can be coated with a porous material, such as a titanium coating. In some embodiments, the surface porosity may be at least approximately 50 microns and less than or equal to approximately 300 microns.

The upper structure 302 can be configured to slideably fit with the lower structure 304. For example, in the embodiment illustrated in FIG. 21 the upper structure 302 has smooth surfaces on its sides that slide against smooth surfaces on the sides of the lower structure 304 to form a slide bearing. In other embodiments, the upper structure and lower structure can have any of a plurality of different types of functional couplers to form a slideable connection.

Figure 21:
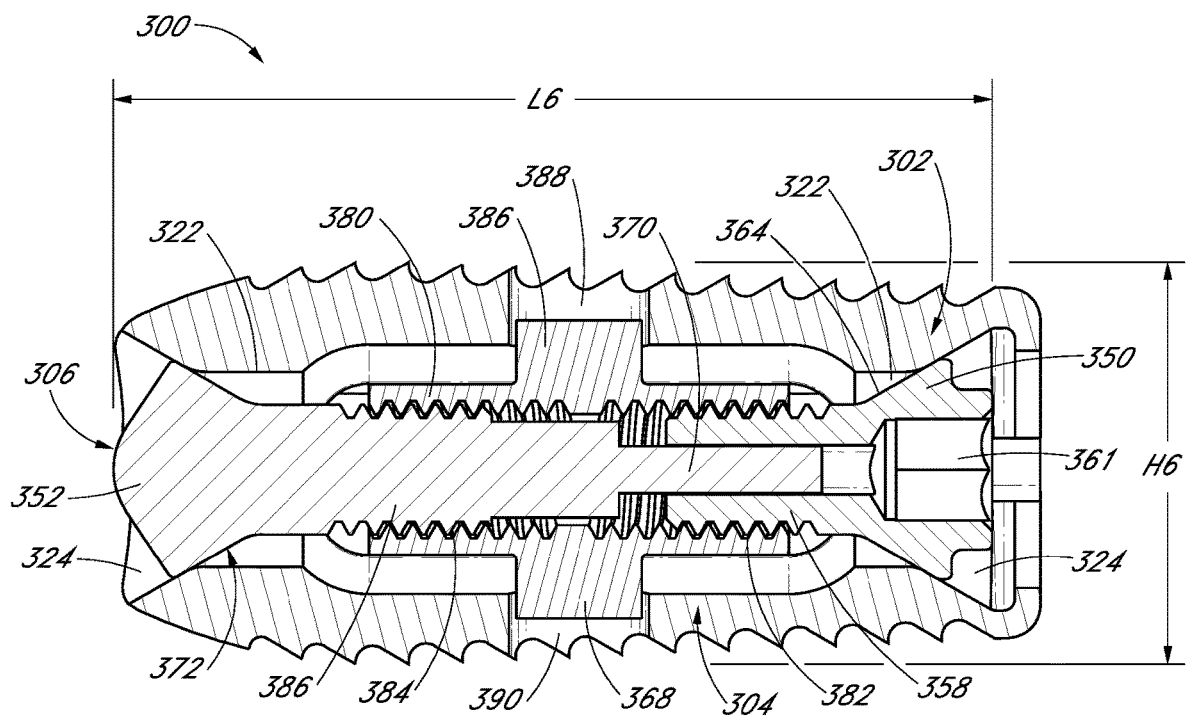
FIG. 21 is a cross-sectional view of the expandable interbody device of FIG. 18 in an expanded configuration.

The distal sides 312, 330 and the proximal sides 314, 332 of the top surface 308 and bottom surface 328 can have a screw opening 322 that accepts the screw mechanism 306, as illustrated in FIG. 21. The outer surfaces of the screw opening 322 can have an angled surface 324. The angled surface 324 can flare outward toward the surface, such that the screw opening 322 is larger at the surface of the distal side or proximal side than the opening in toward the middle. When the upper structure 302 and the lower structure 304 are in the collapsed configuration, the angled surfaces 324 can form a frustoconical shape. The upper structure 302 can have approximately half of the cone and the lower structure can have approximately half of the cone. The angled surfaces 324 can interface with the screw mechanism 306 to transition the interbody device 300 from the collapsed to expanded configuration, as explained below.

Figure 19:
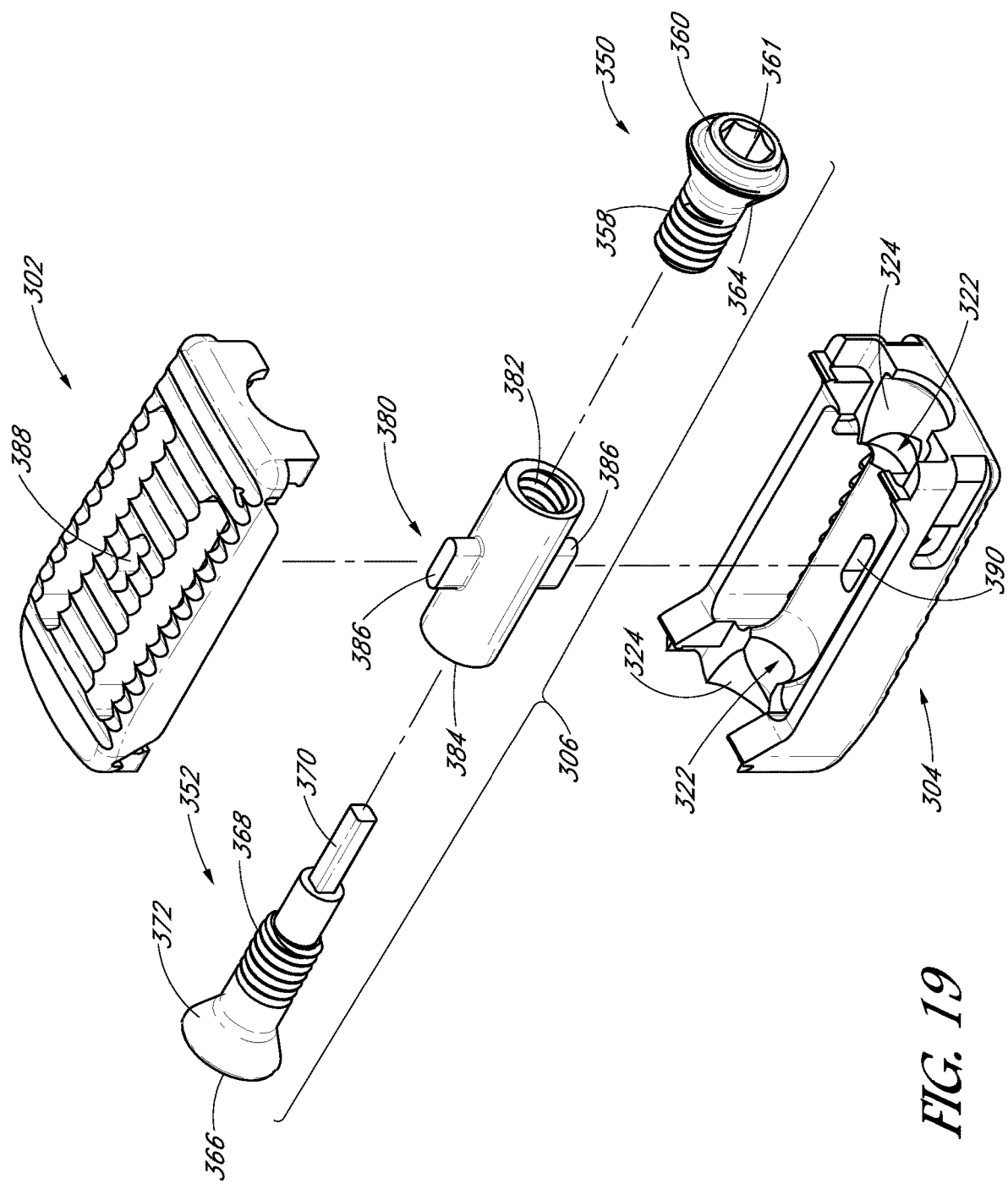
FIG. 19 is a perspective exploded view showing the expandable interbody device of FIG. 12, including the upper structure, lower structure and screw mechanism.

With reference to FIG. 19, the screw mechanism 306 can include a proximal section 350, a distal section 352 and a coupler 380. The coupler 380 can have a proximal hole 382 configured to engage the proximal section 350 and a distal hole 384 configured to engage the distal section 352. The holes 382, 384 can have threads in opposite directions (i.e., one having a left hand thread and the other a right hand thread). The proximal section 350 can have threads that are configured to engage threads in the proximal hole 382 and the distal section 352 can have threads that are configured to engage threads in the distal hole 384. In the illustrated embodiment, the proximal section 350 and distal section 352 have external threads while the coupler 380 has internal threads. In other embodiments, the coupler can have external threads while the proximal section and distal section have internal threads. As discussed in more detail below, the threads in opposite directions enable the screw mechanism 306 to contract or extend when rotated.

The coupler 380 can include protrusions 386 configured to engage with apertures 388, 390 in the upper structure 302 and lower structure 304, respectively, to prevent the coupler 380 from rotating as the proximal section 350 of is rotated with a drive tool. In the illustrated embodiment of FIGS. 12-19, the coupler 380 includes two protrusions 386 having oval shaped extensions that fit into oval-shaped apertures 388, 390. In other embodiments, the protrusions can have any of a variety of shapes, such as cylindrical or rectangular extensions.

The proximal section 350 can include a threaded portion 358 configured to engage the threads on the proximal hole 382 of the coupler 380. The proximal end of the proximal section 350 can include a head 360 with a drive interface 361 adapted to receive a driving tool for rotating or driving the proximal section 350. In the illustrated embodiment, the head 360 has a hexagonal shaped cavity for receiving a hexagonal drive wrench. In other embodiments, the head can have any of a variety of drive interfaces, such as slotted, cross and polygonal heads. The distal end of the proximal section 350 can have a bore 356 extending along its longitudinal axis configured to receive a shaft 370 of the distal section 352. The distal facing side of the head 360 can have an angled surface 364 configured to slide and press against the angled surfaces 324 of the upper structure 302 and lower structure 304. For example, the angled surface 364 can be a tapered cylindrical surface (i.e., a frustoconical shape as illustrated in FIG. 19), with sufficient smoothness to functionally slide and press against the angled surfaces 324.

The distal section 352 can include a head 366 and a threaded portion 368 configured to couple with the distal hole 384 of the coupler 380. The distal section 352 can also have a shaft 370 extending proximally along the longitudinal axis that is configured to slideably couple with the bore 356 of the proximal section 350. As described below, the shaft 370 and bore 356 can be keyed, such that when the proximal section 350 is rotated, the distal section 352 also rotates as a unit. The proximal facing side of the head 366 can have an angled surface 372 configured to slide against the angled surfaces 324 of the upper structure 302 and lower structure 304, as illustrated in FIGS. 20 and 21.

The proximal section 350 and the distal section 352 can be rotatably linked with a keyed coupling, such that when the proximal section 350 is rotated, the distal section 352 also rotates as a unit. The shaft 370 on the distal section 352 can have a keyed shape that slideably engages with the bore 356, on the proximal section 350, which has a matching keyed shape. In the embodiment illustrated in FIG. 21, the shaft 370 has a square cross-sectional shape that slideably engages a bore 356 having a square cross-sectional shape. Other suitable shapes or geometric configurations for a keyed connection between the proximal section 350 and distal section 352 may be used in the screw mechanism 306 to achieve the desired results, such as triangular, hexagonal, oval, star-shaped, or other non-circular shape.

In use, the drive interface 361 can be actuated to compress the screw mechanism 306, which engages the upper structure 302 and lower structure 304 to move the two structures away from each other from the collapsed configuration to the expanded configuration. If desired, the drive interface 361 may be actuated in the opposite direction to change the interbody device 300 from the expanded configuration back to the collapsed configuration. This allows the expandable interbody device 300 to be moved to another location or repositioned if it is expanded in the wrong location and needs to be collapsed prior to moving or repositioning.

Figure 20:
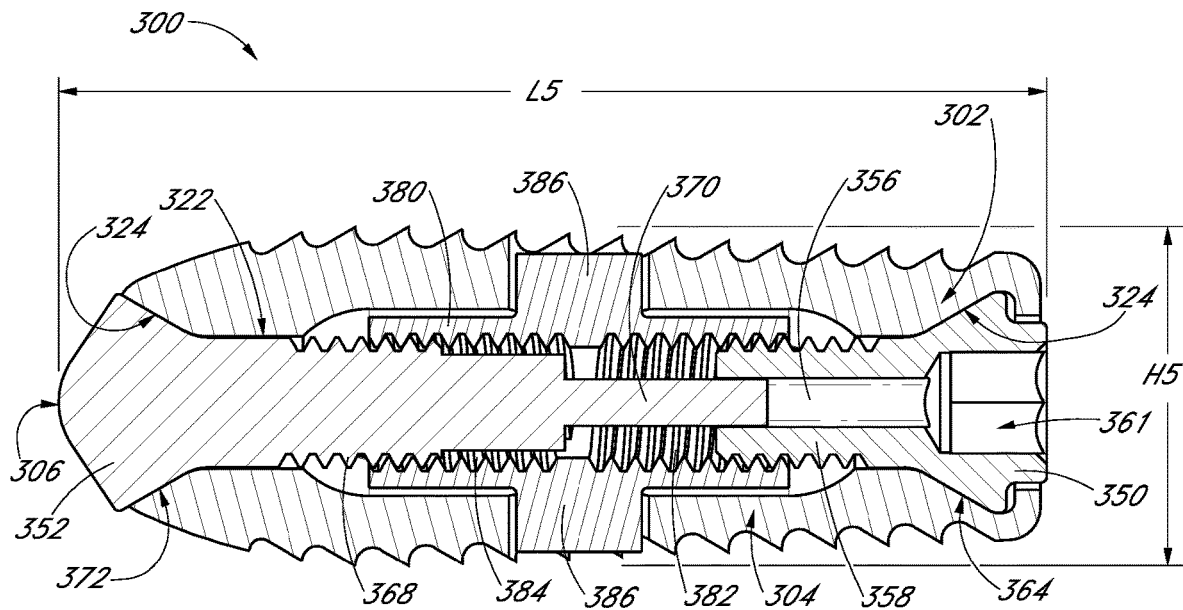
FIG. 20 is a cross-sectional view of the expandable interbody device of FIG. 12 in a collapsed configuration.

With reference to FIGS. 20 and 21, the screw mechanism 306 can vary in length to change the interbody device from the collapsed configuration to the expanded configuration. Initially, the length of the screw mechanism 306 can be L5 in the collapsed configuration, shown in FIG. 20. As the drive interface 361 is rotated in a first direction, the proximal section 350 and the distal section 352 are screwed into the coupler 380 and the length of the screw mechanism 306 contracts to L6 in the expanded configuration, shown in FIG. 21. The protrusions 386 on the coupler 380 are constrained in the apertures 388, 390 on the upper structure 302 and lower structure 304 to prevent the coupler 380 from rotating with the proximal section 350 and distal section 352 as the drive interface 361 is rotated. By reversing rotation of the drive interface 361 in a second direction, opposite the first, the screw mechanism 306 can be extended in length from L6 back to L5, if desired.

In the embodiment illustrated in FIGS. 20 and 21, in the collapsed configuration the expandable interbody device 300 has a distance of H5. The angled surface 364 of the proximal section 350 can contact the proximal ramp portions 324 of the upper structure 302 and lower structure 304. The angled surface 372 of the distal section 352 can engage the distal ramp portions 324 of the upper structure 302 and lower structure 304. When the drive interface 361 is rotated in a first direction, the proximal section 350 and the distal section 352 can move toward each other from L5 to L6, as explained above. When this happens, the angled surfaces 364 and 372 can push against the angled surfaces 324 of the upper structure 302 and lower structure 304, causing the upper structure 302 and lower structure 304 to separate. The distance between the upper structure 302 and the lower structure 304 can increase from H5 (collapsed configuration) to H6 (expanded configuration). The expandable interbody device 300 does not have to be completely expanded to H6 and may only be expanded to a partial distance between H5 and H6, depending on the expansion needed between the adjacent vertebrae. The proximal and distal angled surfaces 324 can have features that increase resistance to turning of the screw mechanism 306, so that increased actuating forces are required during select portions of the expansion procedure. This variation of actuating forces can provide tactile feedback to the surgeon as an indication of expansion position of the expandable interbody device 300, such as when the interbody device 300 is nearing the limits of its expansion.

As mentioned above, the threaded portion 358 of the proximal section 350 can engage with the proximal hole 382 of the coupler 380 and the threaded portion 368 of the distal section 352 can engage with the distal hole 384 of the coupler 380. The proximal hole 382 and distal hole 384 can have thread patterns in opposite directions and the thread portions 358, 368 can have corresponding thread patterns in opposite directions. In some embodiments, the proximal and distal holes 382, 384 and the thread portions 358, 368 may have equal pitch, such that during expansion, the proximal side and distal side of the upper structure 302 and lower structure 304 translate or move at the same rate. In other embodiments, the proximal hole 382 and threaded portion 358 of the proximal section 350 may have a different pitch than the distal hole 384 and threaded portion 368 of the distal section 352, such that during expansion, the proximal side and distal side of the upper structure 302 and lower structure 304 translate or move at different rates. For example, the proximal side of the upper structure 302 and lower structure 304 may translate or move at a first rate of speed and the distal side of the upper structure 302 and lower structure 304 may translate or move at a second rate of speed. The first rate of speed may be faster or slower than the second rate of speed. This allows for some angularity between the upper structure 302 and lower structure 304 during expansion. The difference between the first and second rates of speed allows the user to select an expandable interbody device that has some angulation after expansion, for example to account for the lordotic curvature of the spine.

The screw mechanism 306 or portions of the screw mechanism 306 can be fabricated from any biocompatible material suitable for implantation in the human spine, such as metals including, but not limited to, stainless steel, titanium and titanium alloys, as well as surgical grade plastics, plastic composites, ceramics, bone, and other suitable materials. In some embodiments, the proximal section 350 and the distal section 352 may be formed of a porous material that participates in the growth of bone with the adjacent vertebral bodies. In some embodiments, the screw mechanism 306 can include a roughened surface that is coated with a porous material, such as a titanium coating, or the material may be chemically etched to form pores that participate in the growth of bone with the adjacent vertebra. In some embodiments, only portions of the screw mechanism 306 may be formed of a porous material, coated with a porous material, or chemically etched to form a porous surface, such as the head 360 of the proximal section 350 and head 366 of the distal section 352, which may be exposed to the native anatomy after implant. In some embodiments, the surface porosity may be between 50 and 300 microns.

In some embodiments, the screw mechanism may be a compression screw having a proximal section threadably coupled to a distal section, the proximal section having a threaded shaft and the distal section having a threaded bore, or vice-versa, such that when the proximal section is rotated, the threaded shaft engages the threaded bore to shorten or lengthen the distance between the proximal head and the distal head. The distal section can have anti-rotational features, such as for example an oblong head shape, to prevent it from rotating as the proximal section is engaged with distal section.

Figure 22:
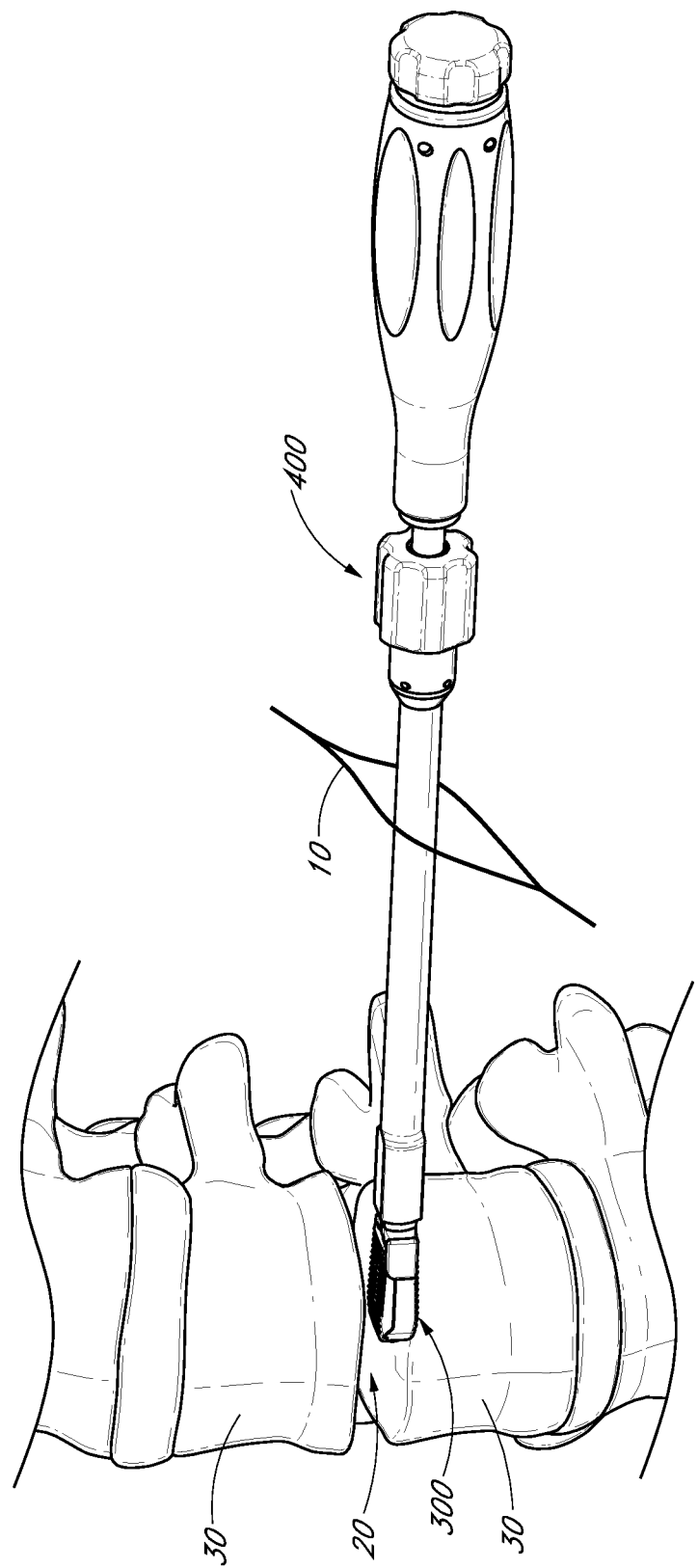
FIG. 22 is a perspective view of the expandable interbody device of FIG. 18 coupled to a deployment tool and being implanted between adjacent vertebrae.

With reference to FIG. 22, a deployment tool 400 can be used to implant the interbody device 300 into the patient. In use, an incision 10 can be made on the patient to allow access to the implant site in the intervertebral space 20. The incision can be made for implanting the device from the posterior, lateral or anterior directions. The incision can be small for a minimally invasive procedure or a larger incision can be used for an open surgery. Once the implant site is accessed, the two adjacent vertebrae 30 can be distracted in some situations to open up the intervertebral space 20. In some situations, the expandable interbody device 300 can be used to at least partially distract the vertebrae during the implant procedure. In some situations, the intervertebral space 20 may include a degenerated disc or other disorder that may require a partial or complete discectomy prior to insertion of the expandable interbody device 300.

In some configurations, more than one expandable interbody device 300 can be implanted between the adjacent vertebrae of the patient. In such embodiments, multiple expandable interbody devices 300 can be placed in a side-by-side configuration or any other suitable configuration, thereby creating additional support.

Figure 23:
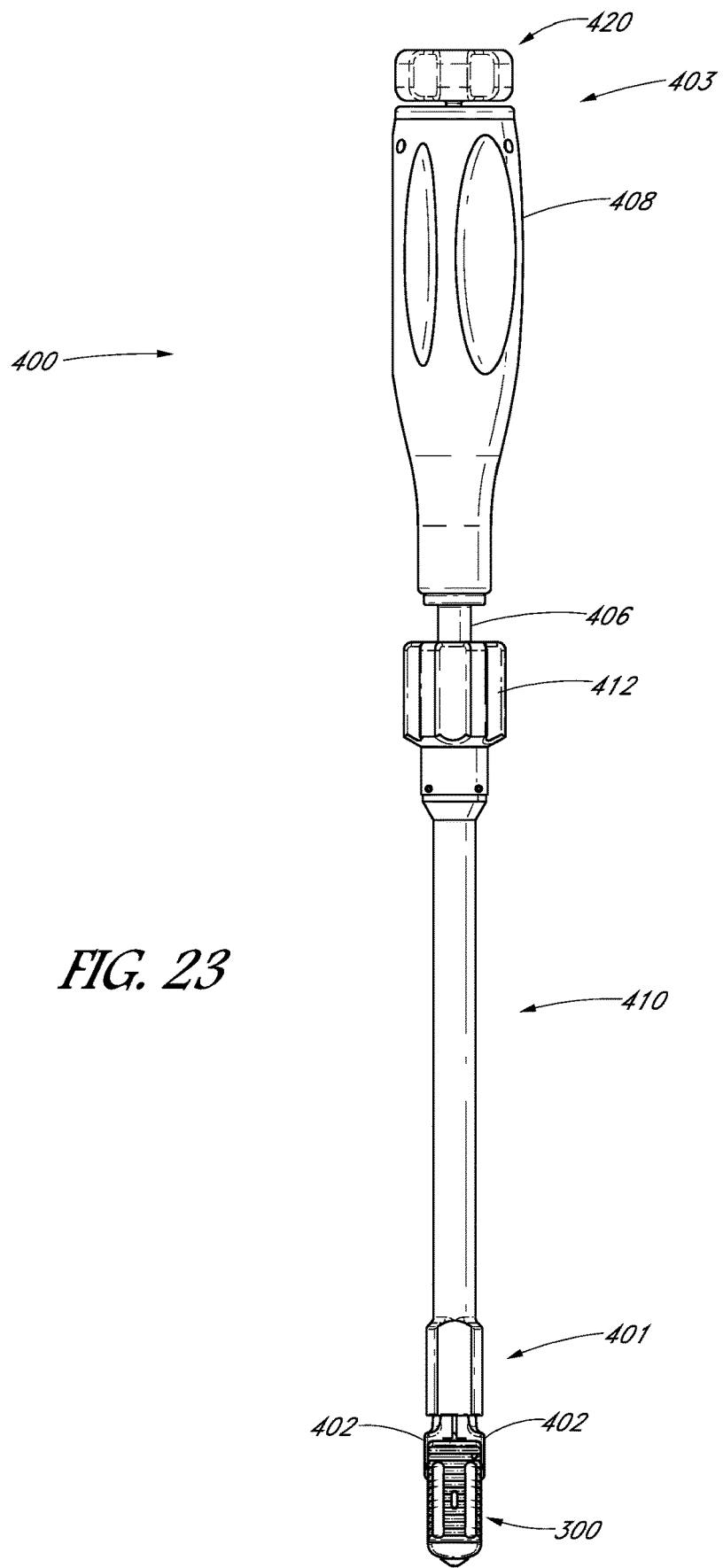
FIG. 23 is a top view of the expandable interbody device and deployment tool of FIG. 22.

With reference to FIG. 23, the deployment tool 400 can have an elongate shaft 406 with a coupling feature toward the distal side 401 that is configured to secure an interbody device 300. The proximal side 403 of the deployment tool 400 can include a handle 408 attached to the shaft 406. A hollow sleeve 410 can be disposed over the shaft 406 such that the longitudinal axis of the shaft 406 is generally coincident with the longitudinal axis of the sleeve 410. The sleeve 410 is movably attached to the shaft 406 and is configured to translate along the longitudinal axes. An actuation device 420 can extend through the length of the deployment tool 400 such that a drive of the actuation device 420 is at the distal side 401 and a knob is toward the proximal side 403.

Figure 25A:
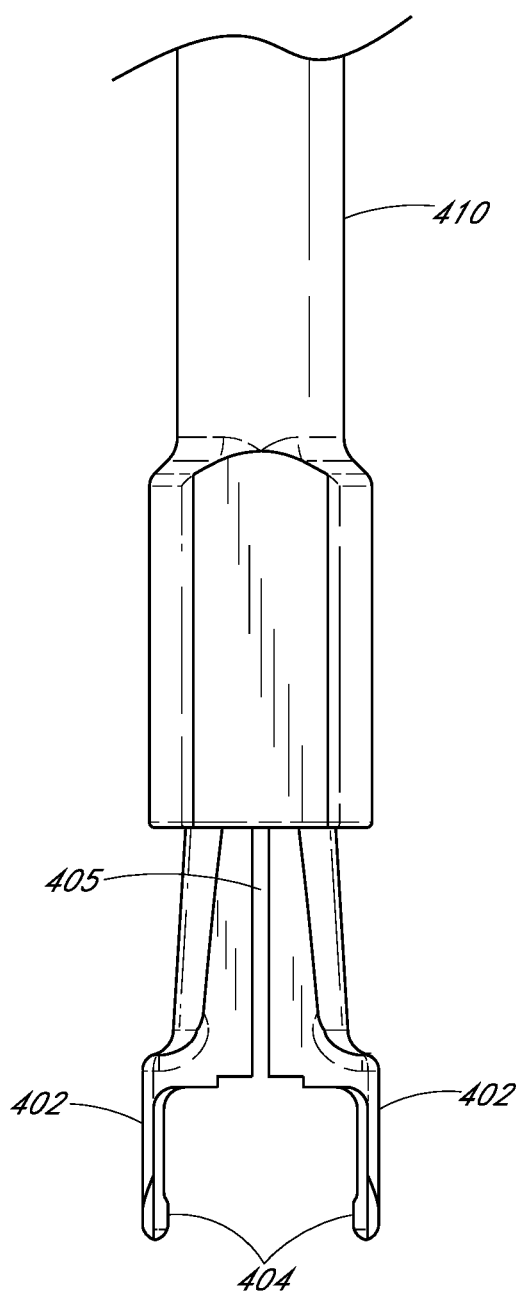
FIG. 25A is a close-up top view of the arms of the deployment tool of FIG. 22 in an open configuration.
Figure 25B:
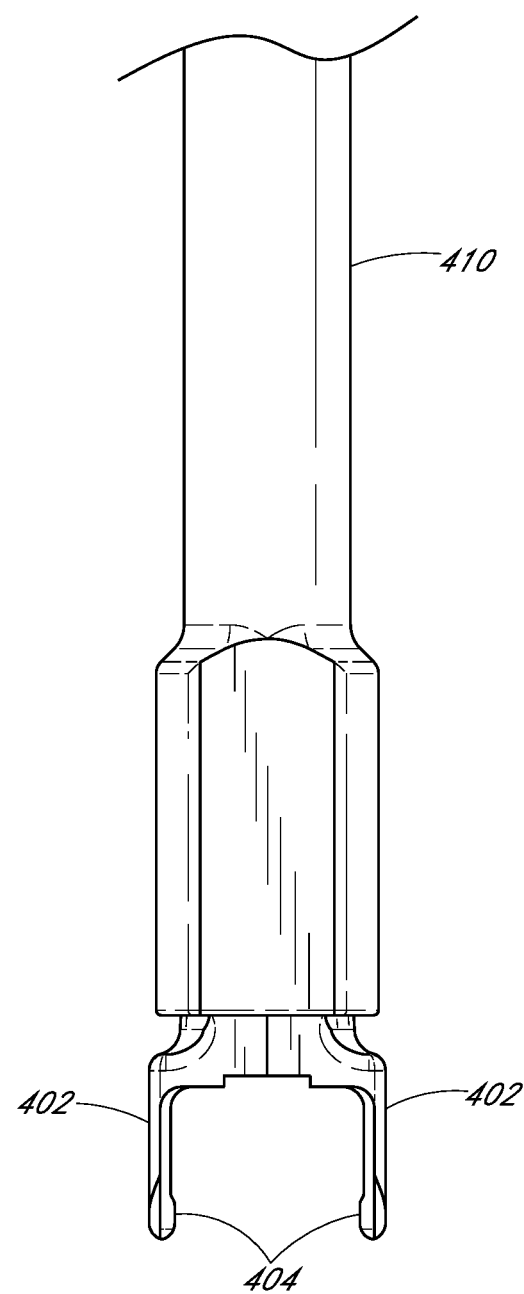
FIG. 25B is a close-up top view of the arms of the deployment tool of FIG. 22 in a closed configuration.

The coupling feature includes arms 402 or clamps that engage with the recesses 320 of the lower structure 304 of the interbody device 300. As shown in the close-up views of FIGS. 25A-B, the arms 402 can have protrusions 404 that are configured to be retained by the recesses 320 of the interbody device 300. The arms 402 can be moved from an open configuration to a closed configuration by manipulation of a translation mechanism 412. In the open configuration, illustrated in FIG. 25A, the sleeve 410 is in its proximal position, allowing the arms 402 to be spread apart sufficiently to fit around the interbody device 300. In the closed configuration, illustrated in FIG. 25B, the sleeve 410 is in its distal position and the walls of the sleeve 410 can compress the arms 402 together around the interbody device 300. FIG. 26 shows a close-up view of the arms 402 of the deployment tool 400 coupled to a interbody device 300. The arms 402 can have protrusions 404 that engage the recesses 320 on the interbody device 300. In some configurations, the arms 402 can have rails that engage with slots on the interbody device 300.

In other embodiments, the deployment tool can be coupled to the interbody device through other mechanisms, such as rotational (e.g., threaded) engagement, temporary adhesives, clips, hooks, and the like. The deployment tool 400 can include any of a variety of suitable attachment features to couple the deployment tool 400 to the interbody device 300.

Figure 24:
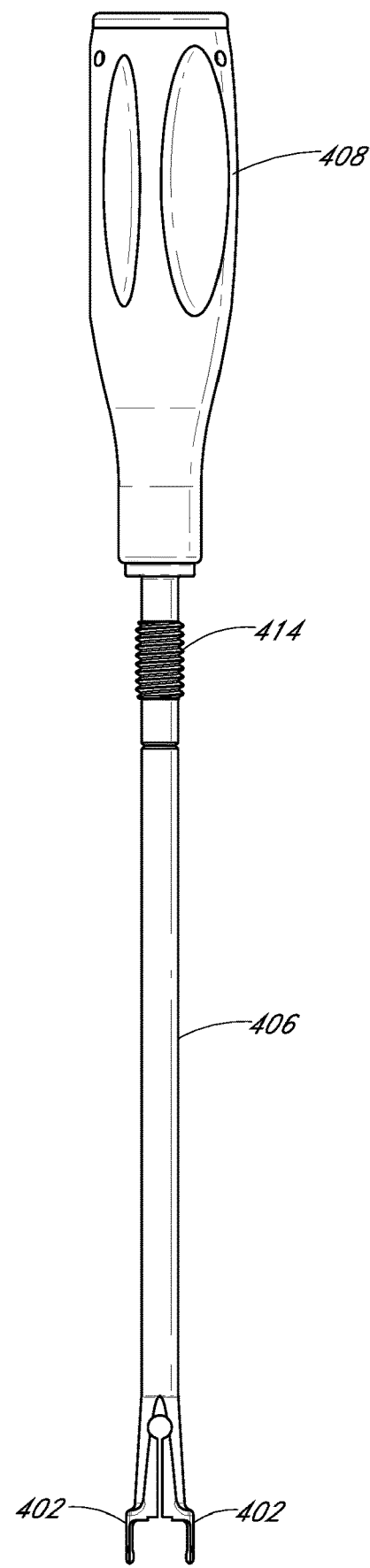
FIG. 24 is a top view of the shaft, handle and arms of the deployment tool of FIG. 22.

With continued reference to FIG. 23, the sleeve 410 can have a translation mechanism 412 toward the proximal end that is configured to actuate the coupling feature. In the illustrated embodiment, the translation mechanism 412 is manipulated by rotation to move the sleeve 410 longitudinally relative to the shaft 406. In some configurations, the translation mechanism 412 and the distal part of the sleeve 410 can be rotatably coupled such that rotation of the translation mechanism 412 is translated to linear movement of the distal part of the sleeve 410. In other configurations, the translation mechanism 412 may be rigidly connected to the distal part of the sleeve 410 such that the entire sleeve 410 rotates as it translates. The inner surface of the translation mechanism 412 can have threads that engage threads 414 on the shaft 406, as illustrated in FIG. 24. The threaded coupling between the shaft 406 and the sleeve 410 may provide increased mechanical advantage for securing the arms 402 around the interbody device 300.

In some configurations, the sleeve 410 can be slideably connected to the shaft 406, in which case the sleeve 410 is manipulated by pushing and pulling. Other means of coupling the sleeve to the shaft such that an actuation of the translation mechanism results in a desired corresponding movement of the sleeve are possible and are considered within the scope of the disclosure. The deployment tool 400 can be straight or curved or a combination of these shapes. In some configurations, the deployment tool can have a variable angle shaft such that the shape of the tool can be adjusted during use. For example, the deployment tool can have a hinge that adjusts the bend angle of the shaft for improved fitment of the deployment tool through the incision and to the target implant site. The deployment tool 400 can be stiff, bendable, or partially stiff and partially bendable. In still other embodiments, a power source may be provided for hydraulic, pneumatic or other power-assisted manipulation of the sleeve 410.

Figure 27:
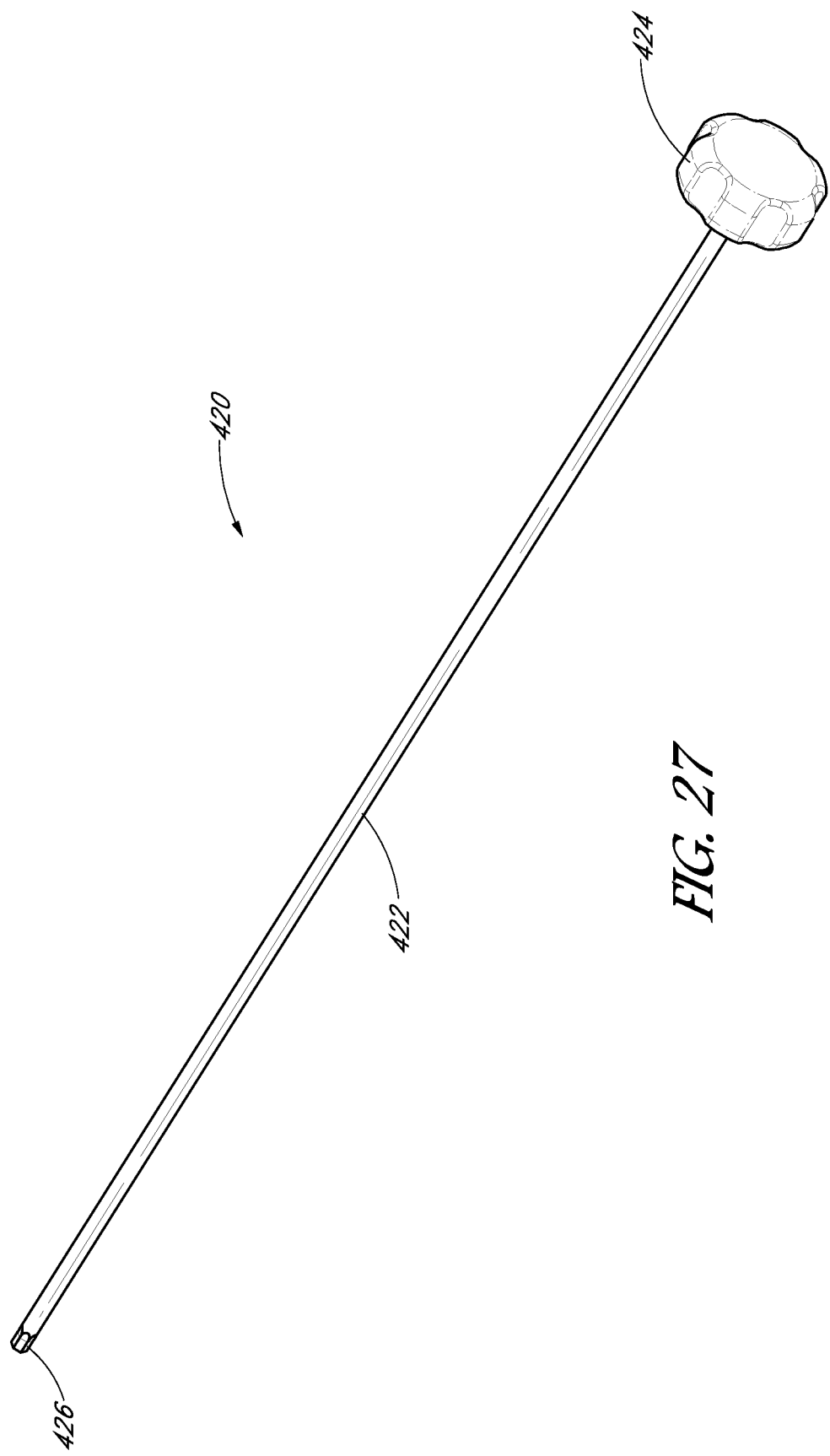
FIG. 27 is a perspective view of an actuation device of the deployment tool of FIG. 22.

With continued reference to FIG. 23, the deployment tool 400 can include an actuation device 420 that extends the length of the deployment tool 400 for actuating the drive interface 361 from the proximal portion of the deployment tool 400. The actuation device 420 can have a distal portion configured to engage the drive interface 361 of the proximal section 350 of the screw mechanism 306, and a proximal portion for actuation. For example, the embodiment illustrated in FIG. 27 shows an actuation device 420 with an elongate shaft 422 that extends the length of the deployment tool 400. A knob 424 can be disposed at the proximal end of the shaft 422 to enable the user to rotate the actuation device 420. In other configurations, the proximal end can have a lever, flat protrusion, drive interface or other suitable rotational mechanism for manipulating the actuation device. The distal end of the shaft 422 can have a drive 426 configured to engage the drive interface 361. For example, the drive 426 can be a hexagonal-shaped driver, or any other shape that is complementary to the drive interface 361 cavity of the screw mechanism 306.

Figure 28:
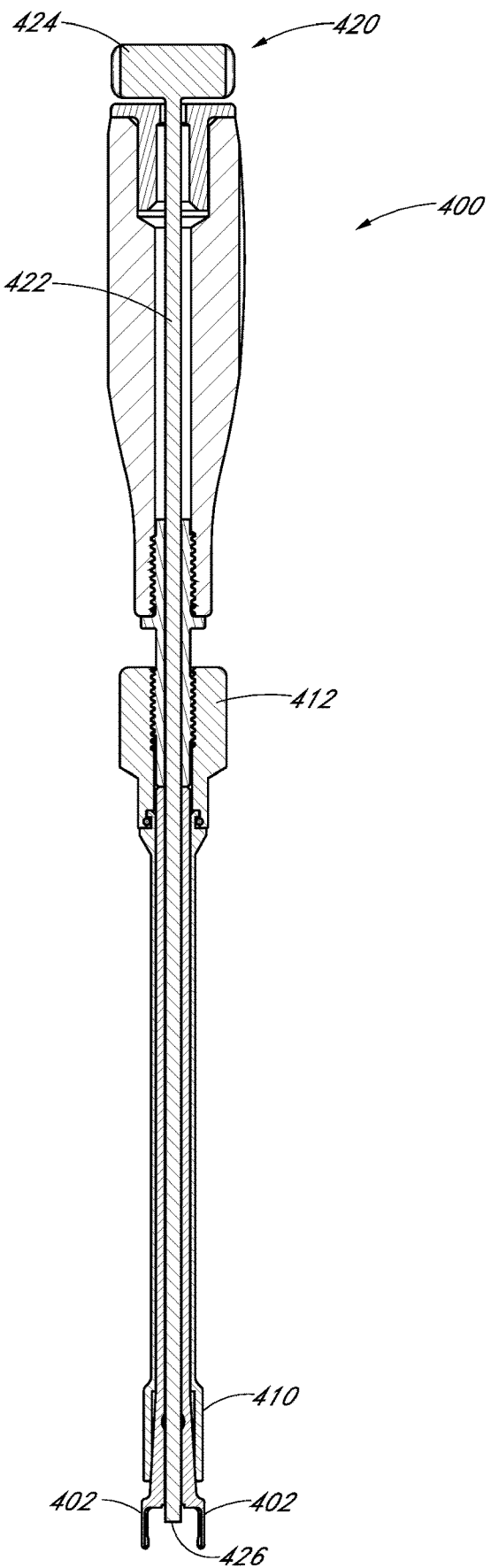
FIG. 28 is a cross-sectional top view of the deployment tool of FIG. 22.

In operation, the actuation device 420 can be placed through a passageway extending through the center of the deployment tool 400, as illustrated in the cross-sectional view of FIG. 28. After the expandable interbody device 300 is inserted and positioned within the intervertebral space 20 between two vertebrae 30, the actuation device 420 can be used to deploy and expand the expandable interbody device 300 by applying a rotational force to the actuation device 420. By rotating the knob 424 at the proximal portion of the deployment tool 400, the drive 426 is also rotated, which in turn rotates the drive interface 361 of the screw mechanism 306 and expand the interbody device 300.

As the deployment tool 400 applies the rotational force, the expandable interbody device 300 gradually expands as described above. The interbody device 300 can be expanded until it contacts the two adjacent vertebrae. In some configurations, the interbody device 300 can be used to distract the two adjacent vertebrae and open up the intervertebral space 20. The actuation device 420 can advantageously transmit sufficient torque to the screw mechanism 306 to enable distraction using the interbody device 300. In some configurations, the actuation device 420 can have a torque-limiting feature to prevent over-tightening of the screw mechanism 306. For example, the torque-limiting feature can include a spring-loaded clutch mechanism along the shaft 422 of the actuation device 420 that can only transmit a predetermined amount of torque before the clutch slips. The amount of torque that can be transmitted can depend on the stiffness of the clutch spring. In other embodiments, the torque-limiting feature can be a portion of the shaft 422 that is configured to break at a predetermined torque. In other embodiments, the feature can be any functional torque-limiting device.

In some embodiments, the deployment tool 400 can be used to deliver fluids, medication or other materials, especially materials that can help in the integration of the interbody device with the vertebrae, such as allograft, Demineralized Bone Matrix ("DBM") packing, and/or other bone graft material. The material can also fill up the empty cavity created between the upper structure 302 and lower structure 304 upon expansion, helping to provide support to the vertebrae.

Figure 29:
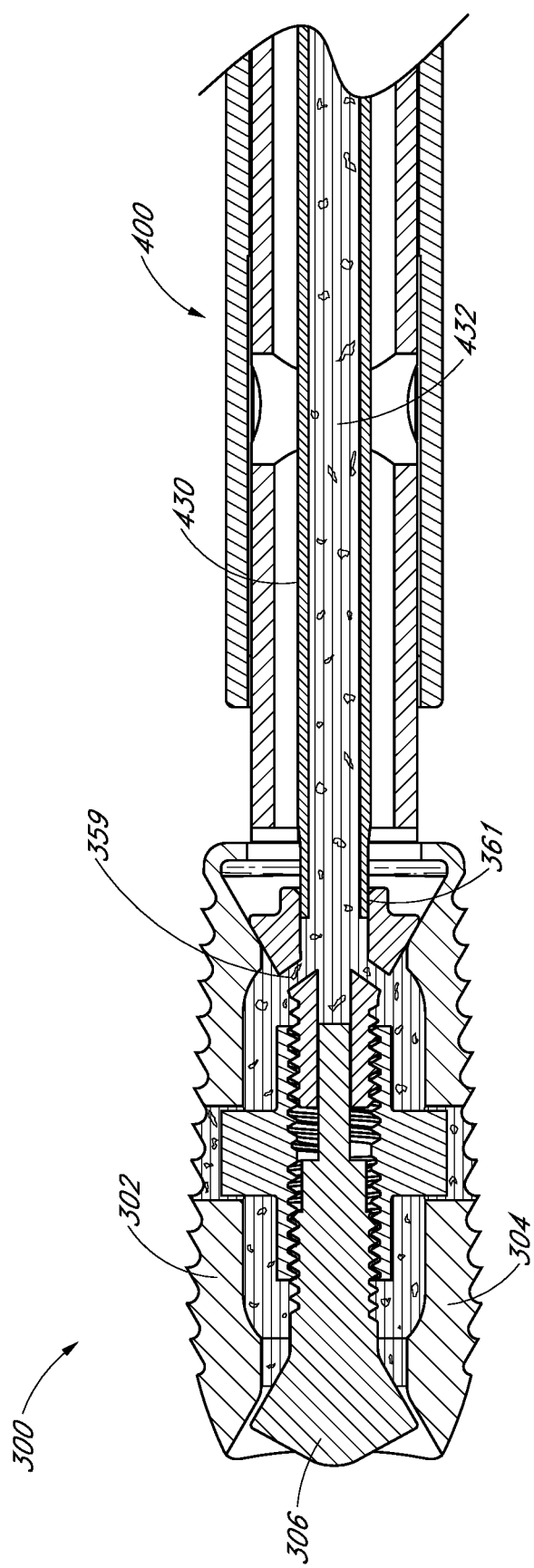
FIG. 29 is a close-up cross-sectional view of the expandable interbody device and deployment tool showing fluid delivery through the screw mechanism.

With reference to FIG. 29, a delivery tube 430 can extend the length of the deployment tool 400 from the proximal side 403 of the deployment tool 400 to the proximal section of the screw mechanism 306. The delivery tube 430 can have a channel 432 extending the length of the delivery tube 430 and open at the distal end so that it is in fluid communication with the drive interface 361 of the proximal section 350 of the screw mechanism 306. In some embodiments, the delivery tube 430 is the same as the actuation device except with a channel extending longitudinally through it. The actuation device 420 can be a separate component that is removed from the deployment tool 400 to insert the delivery tube 430. In some embodiments, the delivery tube 430 and actuation device 420 are the same component that serves both functions. For example, the actuation device can have a distal end configured to engage the drive interface 361 and a channel extending through its length.

In some configurations, the material is forced through the delivery channel 432 by a pressurized delivery system. For example, a powered compressor can be attached to the proximal end of the delivery tube 430 to push material through the delivery channel 432 and into the cavity of the interbody device 300. In some configurations, the fluids, medication or other material is delivered to the interbody device 300 by manually pushing the material through the delivery tube, for example by using a push rod. The push rod can be an elongate shaft that closely fits the inside diameter of the delivery channel. The push rod can have a force multiplier to provide increased mechanical advantage for pushing the material through the delivery channel. For example, the push rod can be threadedly engageable with the delivery tube such that the material is pressed through the delivery channel as the push rod is screwed onto the delivery tube. In another example, the push rod can include a ratcheting handle that provides leverage to help push material through the delivery channel.

Figure 30:
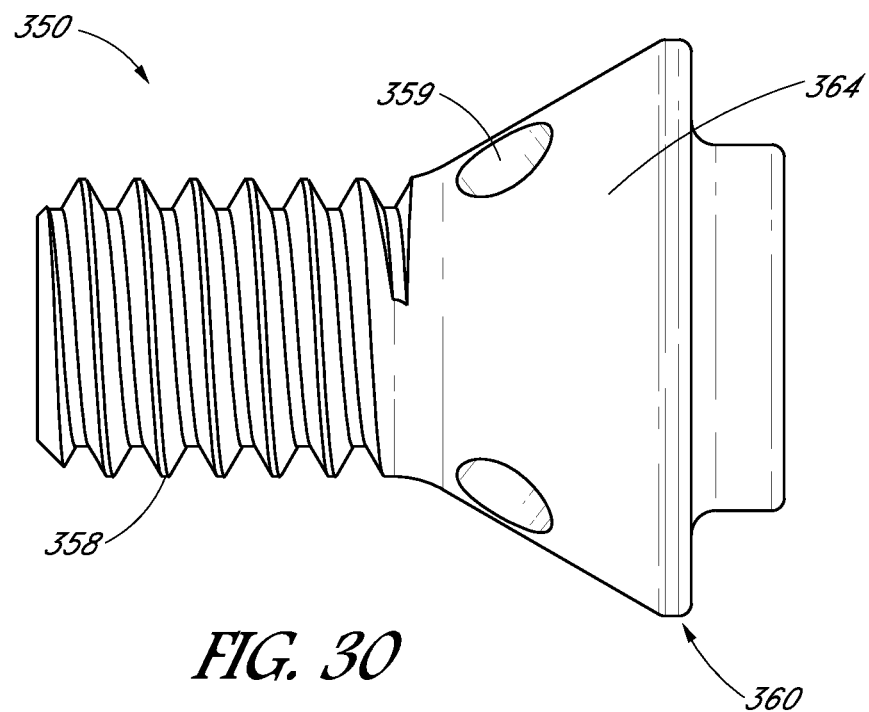
FIG. 30 is a side view of the proximal section of the screw mechanism of FIG. 19.
Figure 31:
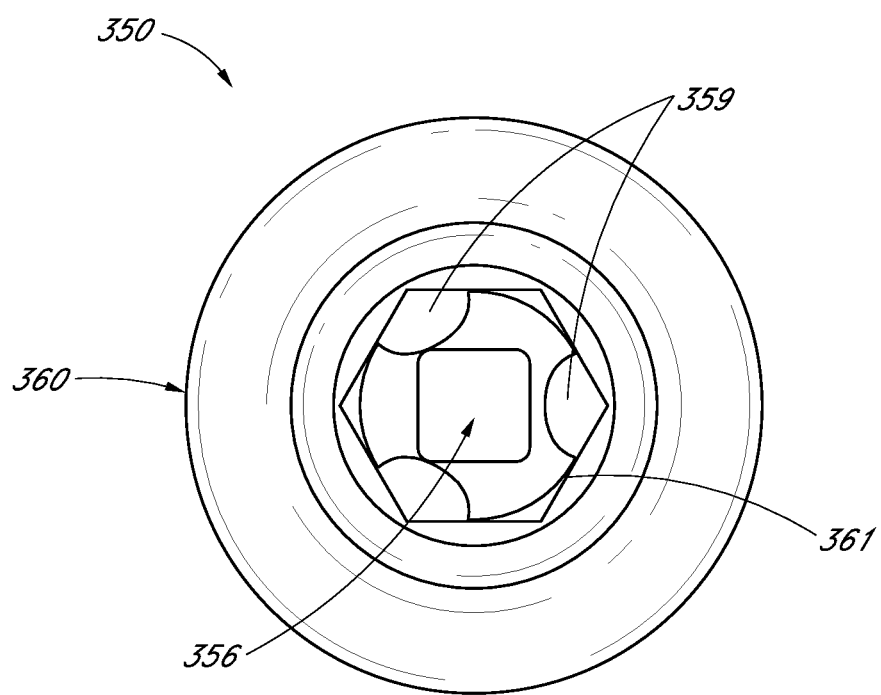
FIG. 31 is a rear view of the proximal section of the screw mechanism of FIG. 19.

With reference to FIGS. 30 and 31, the proximal section 350 of the screw mechanism can have injection holes 359 that extend from the drive interface 361 to the angled surface 364. The proximal section 350 can have one, two, three, or more injection holes 359. In the illustrated embodiment, the injection holes 359 are round holes. In other embodiments, the injection holes can be any of a variety of shapes, such as square, oval or polygonal. The injection holes can provide fluid communication between the delivery channel 432 and the interior of the interbody device 300. In the illustrated embodiment of FIG. 23, the delivered material travels through the channel 432, into the drive interface 361, through the injection holes 359 and into the cavity between the upper structure 302 and lower structure 304. The material can fill up the cavity and also travel through the slots 318 in the upper structure 302 and the slots 336 in the lower structure 304 to come into contact with the vertebrae.

Figure 32:
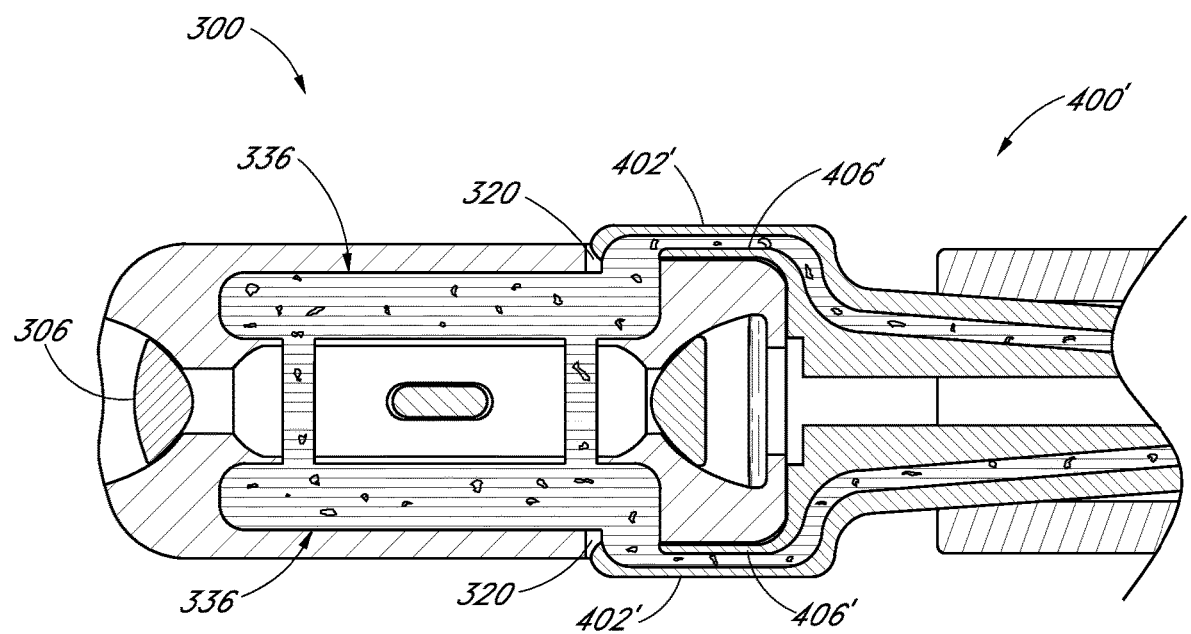
FIG. 32 is a cross-sectional view of the expandable interbody device and deployment tool showing fluid delivery through channels in the delivery tool, according to another embodiment of the present invention.

As illustrated in cross-sectional top view of FIG. 32, the fluids, medication or other materials can be delivered through the arms 402' of the deployment tool 400'. Channels 432' can extend through the arms 402' and have an opening at the tips of the arms 402'. When the deployment tool 400' is coupled with the interbody device 300, the opening in the arms 432' can be positioned in the recesses 320 of the lower structure 304, placing the channels 432' in fluid communication with the interior cavity of the interbody device 300. This configuration advantageously allows the materials to be delivered to the interbody device 300 through existing components without having to introduce a separate pathway.

The deployment tool can be made of any appropriate material for the particular part. Materials can include, but are not limited to, stainless steel, surgical steel, cutlery steel, tool steel, cobalt and its alloys, nickel and its alloys, chromium and its alloys, titanium and its alloys, zirconium and its alloys, aluminum and its alloys, magnesium and its alloys, polymers, elastomers, and ceramics. Ceramics may include, but are not limited to silicon carbide, silicon oxide(s), silicon nitride, aluminum oxide, alumina, zirconia, tungsten carbide, other carbides.

The sizes of the interbody device and deployment tool are appropriate for treating the particular bone. Smaller devices can be used for smaller vertebra and larger devices for larger vertebra. In addition, the device can be used on bones other than the vertebra and on bones for humans and non-humans.

A method of implanting the interbody device 300 comprises coupling the interbody device 300 to the deployment tool 400. The deployment tool 400 can engage the interbody device 300 by manipulating the translation mechanism 412 to clamp the arms 402 onto the recesses 320. An incision 10 can be made on the patient to allow access to the implant site in the intervertebral space 20. The incision can be made for implanting the device from the posterior, lateral or anterior directions. The incision can be small for a minimally invasive procedure or a larger incision can be used for an open surgery. In some situations, two adjacent vertebrae 30 can be distracted to open up the intervertebral space 20. In some configurations, the expandable interbody device 300 can be used to at least partially distract the vertebrae during the implant procedure.

A user can hold the handle 408 of the deployment tool 400 to implant the interbody device 300 in the intervertebral space 20. Once the interbody device 300 is positioned between adjacent vertebrae, the actuation device 420 can be rotated to turn the drive 426 and engage the screw mechanism 306. The screw mechanism 306 changes length from a first length to a second length such that the proximal frustoconical surface 364 engages the upper proximal angled surface and the lower proximal angled surface, and the distal frustoconical surface 372 engages the upper distal angled surface and the lower distal angled surface to expand the upper structure 302 and the lower structure 304 from a first distance to a second distance.

In some embodiments, materials such as fluids, medication, bone graft material, allograft and/or Demineralized Bone Matrix (DBM) can be delivered to the interior cavity of the interbody device 300. The material can be delivered through a delivery tube 430 and into the proximal section 350 of the screw mechanism 306 or through the arms 402 of the deployment tool. In other embodiments, the material can be delivered through other paths to reach the cavity of the interbody device 300.

To release the interbody device 300, the translation mechanism 412 is rotated. Rotation motion of the translation mechanism 412 is transferred to the sleeve 410 as a linear motion away from the arms 402 via the threaded connection. The arms 402 can move apart to release the interbody device 300 and allow removal of the deployment tool 400 from the patient.

In some configurations, more than one expandable interbody device 300 can be implanted between the adjacent vertebrae of the patient. In such embodiments, multiple expandable interbody devices 300 can be placed in a side-by-side configuration or any other suitable configuration, thereby creating additional support.

In some embodiments of the deployment tool 400, the movement of the translation mechanism 412 and/or actuation device 420 can be effected by manual force applied by a person, such as by his or her hands, or alternatively it can be supplied or supplemented with a motor, pneumatics, hydraulics, springs, and/or magnetics. Some embodiments of the tool may comprise a squeeze handle for actuating the tool. Other embodiments of the tool can include closing mechanisms that include compound leverage, ratcheting, and/or multistep closing.

Although certain embodiments, features, and examples have been described herein, it will be understood by those skilled in the art that many aspects of the methods and devices illustrated and described in the present disclosure may be differently combined and/or modified to form still further embodiments. For example, any one component of the device illustrated and described above can be used alone or with other components without departing from the spirit of the present disclosure. Additionally, it will be recognized that the methods described herein may be practiced in different sequences, and/or with additional devices as desired. Such alternative embodiments and/or uses of the methods and devices described above and obvious modifications and equivalents thereof are intended to be included within the scope of the present disclosure. Thus, it is intended that the scope of the present disclosure should not be limited by the particular embodiments described above, but should be determined only by a fair reading of the claims that follow.

What is claimed is:

1. A method of implanting an expandable interbody device comprising:
    positioning the expandable interbody device between adjacent vertebrae, wherein the expandable interbody device comprises:
    an upper structure configured to abut a superior vertebra;
    a lower structure configured to abut an inferior vertebra; and
    a screw mechanism between the upper structure and the lower structure, the screw mechanism comprising a proximal portion, a distal portion and a coupler at least partially between the proximal portion and the distal portion; and
    rotating the proximal portion and the distal portion as a unit to change a length of the screw mechanism from a first length to a second length, wherein the coupler is prevented from rotating by at least one anti-rotational feature when the proximal portion and the distal portion are rotated;
    wherein a distance between the upper structure and the lower structure changes from a first height to a second height as the length of the screw mechanism changes from the first length to the second length.

2. The method of claim 1, wherein the first height corresponds to a collapsed configuration with the upper structure proximate the lower structure and the second height corresponds to an expanded configuration with the upper structure distanced from the lower structure.

3. The method of claim 1, wherein the proximal portion comprises a proximal frustoconical surface, the distal section comprises a distal frustoconical surface, and the coupler comprises a proximal side configured to engage the proximal section and a distal side configured to engage the distal section.

4. The method of claim 1, wherein the proximal portion comprises first threads wound in a first direction configured to engage a proximal threaded hole in the coupler, and the distal portion comprises second threads wound in a second direction, opposite the first direction, configured to engage a distal threaded hole in the coupler.

5. The method of claim 4, wherein the first threads and the second threads have an equal pitch, such that when the screw mechanism is actuated, a proximal end of the interbody device changes height at a same rate as a distal end of the interbody device.

6. The method of claim 4, wherein the first threads and the second threads have a different pitch, such that when the screw mechanism is actuated, a proximal end of the interbody device changes height at a different rate than a distal end of the interbody device.

7. The method of claim 1, wherein the distal portion comprises a keyed shaft configured to slideably engage with a matching keyed bore on the proximal portion.

8. A method of implanting an expandable interbody device comprising:
    positioning the expandable interbody device between adjacent vertebrae, wherein the expandable interbody device comprises:
    an upper structure configured to abut a superior vertebra;
    a lower structure configured to abut an inferior vertebra; and
    a screw mechanism between the upper structure and the lower structure, the screw mechanism comprising a proximal portion, a distal portion and a coupler at least partially between the proximal portion and the distal portion; and rotating the proximal portion and the distal portion as a unit to change a length of the screw mechanism from a first length to a second length, wherein the coupler is prevented from rotating by at least one anti-rotational feature that engages the upper structure or the lower structure when the proximal portion and the distal portion are rotated;

wherein a distance between the upper structure and the lower structure changes from a first height to a second height as the length of the screw mechanism changes from the first length to the second length.

9. The method of claim 8, wherein the first height corresponds to a collapsed configuration with the upper structure proximate the lower structure and the second height corresponds to an expanded configuration with the upper structure distanced from the lower structure.

10. The method of claim 8, wherein the proximal portion comprises a proximal frustoconical surface, the distal section comprises a distal frustoconical surface, and the coupler comprises a proximal side configured to engage the proximal section and a distal side configured to engage the distal section.

11. The method of claim 8, wherein the proximal portion comprises first threads wound in a first direction configured to engage a proximal threaded hole in the coupler, and the distal portion comprises second threads wound in a second direction, opposite the first direction, configured to engage a distal threaded hole in the coupler.

12. The method of claim 11, wherein the first threads and the second threads have an equal pitch, such that when the screw mechanism is actuated, a proximal end of the interbody device changes height at a same rate as a distal end of the interbody device.

13. The method of claim 11, wherein the first threads and the second threads have a different pitch, such that when the screw mechanism is actuated, a proximal end of the interbody device changes height at a different rate than a distal end of the interbody device.

14. The method of claim 8, wherein the distal portion comprises a keyed shaft configured to slideably engage with a matching keyed bore on the proximal portion.

* * * * *